(12) United States Patent
Yoshida et al.

(10) Patent No.: US 7,482,328 B2
(45) Date of Patent: Jan. 27, 2009

(54) ANTIMICROBIAL POLYPEPTIDE AND UTILIZATION THEREOF

(75) Inventors: Tetsuhiko Yoshida, Nagoya (JP); Masayoshi Kume, Nagoya (JP); Yoshinao Yamada, Nagoya (JP); Yoko Matsuda, Tsukuba (JP); Hiroki Kourai, Tokushima (JP)

(73) Assignee: Toagosei Co., Ltd. (JP)

( * ) Notice: Subject to any disclaimer, the term of this patent is extended or adjusted under 35 U.S.C. 154(b) by 390 days.

(21) Appl. No.: 10/512,299

(22) PCT Filed: Apr. 24, 2003

(86) PCT No.: PCT/JP03/05225

§ 371 (c)(1), (2), (4) Date: Oct. 21, 2004

(87) PCT Pub. No.: WO03/091429

PCT Pub. Date: Nov. 6, 2003

(65) Prior Publication Data

US 2006/0057668 A1 Mar. 16, 2006

(30) Foreign Application Priority Data

Apr. 25, 2002 (JP) ............................. 2002-124830

(51) Int. Cl.
*A61K 38/10* (2006.01)
*A61K 38/16* (2006.01)

(52) U.S. Cl. ........................................ 514/13; 530/326

(58) Field of Classification Search ....................... None
See application file for complete search history.

(56) References Cited

U.S. PATENT DOCUMENTS

| | | | |
|---|---|---|---|
| 5,424,396 A * | 6/1995 | Tomita et al. ................ 530/329 |
| 5,547,939 A | 8/1996 | Selsted | |
| 5,789,542 A | 8/1998 | McLaughlin et al. | |
| 5,807,746 A | 9/1998 | Lin et al. | |
| 5,877,282 A | 3/1999 | Nadler et al. | |
| 5,962,415 A | 10/1999 | Nadler | |
| 6,043,339 A | 3/2000 | Lin et al. | |
| 6,063,612 A * | 5/2000 | Jayasena et al. .......... 435/235.1 |
| 6,180,604 B1 | 1/2001 | Fraser et al. | |
| 6,191,254 B1 | 2/2001 | Falla et al. | |
| 6,303,575 B1 | 10/2001 | Selsted | |
| 6,476,189 B1 | 11/2002 | Yamakawa et al. | |

FOREIGN PATENT DOCUMENTS

| | | |
|---|---|---|
| JP | 2001-186887 | 7/2001 |
| WO | WO 94/02610 A | 2/1994 |
| WO | WO 96/36692 A | 11/1996 |
| WO | WO 98/51794 | 11/1998 |
| WO | WO 99/26971 | 6/1999 |
| WO | WO 99/29721 A | 6/1999 |
| WO | WO 99/67284 A | 12/1999 |
| WO | WO 00/09553 | 2/2000 |
| WO | WO 01/09175 | 2/2001 |
| WO | WO 01/38547 A2 | 5/2001 |
| WO | WO 02/10201 A2 | 2/2002 |

OTHER PUBLICATIONS

Vidal et al. 'Solid Phase Synthesis and Cellular Localization of an C-and/or N-Termial Labelled Peptide.' Journal of Peptide Science, vol. 2, pp. 125-133. 1996.*
Supplementary European Search Report dated Jan. 17, 2006, for European Patent Application No. EP 03 72 5651, 3 pages.
Shai, Yechiel, "From Innate Immunity to de-Novo Designed Antimicrobial Peptides," Current Pharmaceutical Design, 2002, vol. 8, pp. 715-725.
Laure Beven et al., "Effects on mollicutes (wall-less bacteria) of synthetic peptides comprising a signal peptide or a membrane fusion peptide, and a nuclear localization sequence (NLS)—a comparison with melittin," Biochim Biophys Acta Oct. 23, 1997:1329(2), pp. 357-369.
Laurent Chaloin et al., "Ionic channels formed by a primary amphipathic peptide containing a signal peptide and a nuclear localization sequence," Biochim biophys Acta Oct. 15, 1998:1375(1-2), pp. 52-60.
European Examination Report dated Dec. 4, 2006, for European Patent Application No. EP 03 725 651.8-1212, 6 pages.
Nair, R., et al., "NLSdb: Database of Nuclear Localization Signals," Nucleic Acids Research, 31:397-399 (2003).
European Examination Report dated Jul. 13, 2007, for European Patent Application No. EP 03 725 651.8-1212, 5 pages.

* cited by examiner

*Primary Examiner*—Anish Gupta
(74) *Attorney, Agent, or Firm*—Perkins Coie LLP; Lauren Sliger

(57) ABSTRACT

The present invention provides an artificially synthesized antimicrobial polypeptide that does not occur in nature and an antimicrobial agent comprising this polypeptide as the main component. This polypeptide contains in its peptide chain one or more types of nuclear localization signal sequences (NLSs) and/or one or more units of sequences prepared by partially modifying the NLS(s). The one or more units of NLSs and/or modified NLSs contain at least 5 amino acid residues in total and amount to 30% or more of the total amino acid residues constituting the peptide chain.

4 Claims, 8 Drawing Sheets

SEQUENCE LISTING

<160> NUMBER OF SEQ ID NOS: 123

<210> SEQ ID NO 1
<211> LENGTH: 7
<212> TYPE: PRT
<213> ORGANISM: Homo sapiens

<400> SEQUENCE: 1

Arg Arg Met Lys Trp Lys Lys
1               5

<210> SEQ ID NO 2
<211> LENGTH: 7
<212> TYPE: PRT
<213> ORGANISM: Mus musculus

<400> SEQUENCE: 2

Arg Val His Pro Tyr Gln Arg
1               5

<210> SEQ ID NO 3
<211> LENGTH: 24
<212> TYPE: PRT
<213> ORGANISM: Homo sapiens

<400> SEQUENCE: 3

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 4
<211> LENGTH: 7
<212> TYPE: PRT
<213> ORGANISM: Simian virus 40

<400> SEQUENCE: 4

Pro Lys Lys Lys Arg Lys Val
1               5

<210> SEQ ID NO 5
<211> LENGTH: 7
<212> TYPE: PRT
<213> ORGANISM: Saccharomyces cerevisiae

<400> SEQUENCE: 5

Gly Lys Lys Arg Ser Lys Ala
1               5

<210> SEQ ID NO 6
<211> LENGTH: 6
<212> TYPE: PRT
<213> ORGANISM: avian reticuloendotheliosis virus

<400> SEQUENCE: 6

Lys Ala Lys Arg Gln Arg
1               5

<210> SEQ ID NO 7
<211> LENGTH: 8
<212> TYPE: PRT
<213> ORGANISM: Rattus sp.

```
<400> SEQUENCE: 7

Arg Gly Arg Arg Arg Gln Arg
1               5

<210> SEQ ID NO 8
<211> LENGTH: 5
<212> TYPE: PRT
<213> ORGANISM: Rattus sp.

<400> SEQUENCE: 8

Arg Lys Arg Arg Arg
1               5

<210> SEQ ID NO 9
<211> LENGTH: 9
<212> TYPE: PRT
<213> ORGANISM: Homo sapiens

<400> SEQUENCE: 9

Pro Pro Val Lys Arg Glu Arg Thr Ser
1               5

<210> SEQ ID NO 10
<211> LENGTH: 10
<212> TYPE: PRT
<213> ORGANISM: Saccharomyces cerevisiae

<400> SEQUENCE: 10

Pro Tyr Leu Asn Lys Arg Lys Gly Lys Pro
1               5                   10

<210> SEQ ID NO 11
<211> LENGTH: 17
<212> TYPE: PRT
<213> ORGANISM: Homo sapiens

<400> SEQUENCE: 11

Cys Tyr Gly Ser Lys Asn Thr Gly Ala Lys Lys Arg Lys Ile Asp Asp
1               5                   10                  15

Ala

<210> SEQ ID NO 12
<211> LENGTH: 9
<212> TYPE: PRT
<213> ORGANISM: Drosophila sp.

<400> SEQUENCE: 12

Lys Lys Lys Lys Arg Lys Arg Glu Lys
1               5

<210> SEQ ID NO 13
<211> LENGTH: 9
<212> TYPE: PRT
<213> ORGANISM: Drosophila sp.

<400> SEQUENCE: 13

Lys Lys Lys Arg Arg Ser Arg Glu Lys
1               5

<210> SEQ ID NO 14
<211> LENGTH: 18
<212> TYPE: PRT
<213> ORGANISM: Homo sapiens
```

```
<400> SEQUENCE: 14

Lys Val Thr Lys Arg Lys His Asp Asn Glu Gly Ser Gly Ser Lys Arg
1               5                   10                  15

Pro Lys

<210> SEQ ID NO 15
<211> LENGTH: 14
<212> TYPE: PRT
<213> ORGANISM: Rattus sp.

<400> SEQUENCE: 15

Lys Lys Lys Lys Lys Glu Glu Glu Gly Glu Gly Lys Lys Lys
1               5                   10

<210> SEQ ID NO 16
<211> LENGTH: 8
<212> TYPE: PRT
<213> ORGANISM: Borna disease virus

<400> SEQUENCE: 16

Pro Arg Pro Arg Lys Ile Pro Arg
1               5

<210> SEQ ID NO 17
<211> LENGTH: 13
<212> TYPE: PRT
<213> ORGANISM: Borna disease virus

<400> SEQUENCE: 17

Pro Pro Arg Ile Tyr Pro Gln Leu Pro Ser Ala Pro Thr
1               5                   10

<210> SEQ ID NO 18
<211> LENGTH: 20
<212> TYPE: PRT
<213> ORGANISM: Mus musculus

<400> SEQUENCE: 18

Lys Asp Cys Val Ile Asn Lys His His Arg Asn Arg Cys Gln Tyr Cys
1               5                   10                  15

Arg Leu Gln Arg
            20

<210> SEQ ID NO 19
<211> LENGTH: 11
<212> TYPE: PRT
<213> ORGANISM: Polyomavirus sp.

<400> SEQUENCE: 19

Ala Pro Lys Arg Lys Ser Gly Val Ser Lys Cys
1               5                   10

<210> SEQ ID NO 20
<211> LENGTH: 9
<212> TYPE: PRT
<213> ORGANISM: Human immunodeficiency virus

<400> SEQUENCE: 20

Arg Lys Lys Arg Arg Gln Arg Arg Arg
1               5

<210> SEQ ID NO 21
<211> LENGTH: 12
```

```
<212> TYPE: PRT
<213> ORGANISM: Human immunodeficiency virus

<400> SEQUENCE: 21

Arg Gln Ala Arg Arg Asn Arg Arg Arg Trp Arg
1               5                   10

<210> SEQ ID NO 22
<211> LENGTH: 18
<212> TYPE: PRT
<213> ORGANISM: Homo sapiens

<400> SEQUENCE: 22

Met Pro Lys Thr Arg Arg Arg Pro Arg Arg Ser Gln Arg Lys Arg Pro
1               5                   10                  15
Pro Thr

<210> SEQ ID NO 23
<211> LENGTH: 17
<212> TYPE: PRT
<213> ORGANISM: Homo sapiens

<400> SEQUENCE: 23

Lys Arg Pro Met Asn Ala Phe Ile Val Trp Ser Arg Asp Gln Arg Arg
1               5                   10                  15
Lys

<210> SEQ ID NO 24
<211> LENGTH: 5
<212> TYPE: PRT
<213> ORGANISM: Homo sapiens

<400> SEQUENCE: 24

Arg Pro Arg Arg Lys
1               5

<210> SEQ ID NO 25
<211> LENGTH: 17
<212> TYPE: PRT
<213> ORGANISM: Homo sapiens

<400> SEQUENCE: 25

Lys Arg Pro Met Asn Ala Phe Ile Val Trp Ala Gln Ala Ala Arg Arg
1               5                   10                  15
Lys

<210> SEQ ID NO 26
<211> LENGTH: 5
<212> TYPE: PRT
<213> ORGANISM: Homo sapiens

<400> SEQUENCE: 26

Pro Arg Arg Arg Lys
1               5

<210> SEQ ID NO 27
<211> LENGTH: 4
<212> TYPE: PRT
<213> ORGANISM: Arabidopsis sp.

<400> SEQUENCE: 27

Arg Lys Arg Arg
1
```

```
<210> SEQ ID NO 28
<211> LENGTH: 9
<212> TYPE: PRT
<213> ORGANISM: Hepatitis C virus

<400> SEQUENCE: 28

Pro Pro Arg Lys Lys Arg Thr Val Val
1               5

<210> SEQ ID NO 29
<211> LENGTH: 13
<212> TYPE: PRT
<213> ORGANISM: epstein-barr virus

<400> SEQUENCE: 29

Tyr Lys Arg Pro Cys Lys Arg Ser Phe Ile Arg Phe Ile
1               5                   10

<210> SEQ ID NO 30
<211> LENGTH: 13
<212> TYPE: PRT
<213> ORGANISM: epstein-barr virus

<400> SEQUENCE: 30

Leu Lys Asp Val Arg Lys Arg Lys Leu Gly Pro Gly His
1               5                   10

<210> SEQ ID NO 31
<211> LENGTH: 5
<212> TYPE: PRT
<213> ORGANISM: adenovirus

<400> SEQUENCE: 31

Lys Arg Pro Arg Pro
1               5

<210> SEQ ID NO 32
<211> LENGTH: 5
<212> TYPE: PRT
<213> ORGANISM: Saccharomyces cerevisiae

<400> SEQUENCE: 32

Arg Lys Arg Lys Lys
1               5

<210> SEQ ID NO 33
<211> LENGTH: 7
<212> TYPE: PRT
<213> ORGANISM: Homo sapiens

<400> SEQUENCE: 33

Arg Arg Ser Met Lys Arg Lys
1               5

<210> SEQ ID NO 34
<211> LENGTH: 10
<212> TYPE: PRT
<213> ORGANISM: canine parvovirus

<400> SEQUENCE: 34

Pro Ala Lys Arg Ala Arg Arg Gly Tyr Lys
1               5                   10

<210> SEQ ID NO 35
```

-continued

```
<211> LENGTH: 17
<212> TYPE: PRT
<213> ORGANISM: Homo sapiens

<400> SEQUENCE: 35

Arg Lys Cys Leu Gln Ala Gly Met Asn Leu Glu Ala Arg Lys Thr Lys
1               5                   10                  15

Lys

<210> SEQ ID NO 36
<211> LENGTH: 17
<212> TYPE: PRT
<213> ORGANISM: Homo sapiens

<400> SEQUENCE: 36

Arg Arg Glu Arg Asn Lys Met Ala Ala Ala Lys Cys Arg Asn Arg Arg
1               5                   10                  15

Arg

<210> SEQ ID NO 37
<211> LENGTH: 17
<212> TYPE: PRT
<213> ORGANISM: Homo sapiens

<400> SEQUENCE: 37

Lys Arg Met Arg Asn Arg Ile Ala Ala Ser Lys Cys Arg Lys Arg Lys
1               5                   10                  15

Leu

<210> SEQ ID NO 38
<211> LENGTH: 17
<212> TYPE: PRT
<213> ORGANISM: Homo sapiens

<400> SEQUENCE: 38

Lys Lys Ser Lys Lys Gly Arg Gln Glu Ala Leu Glu Arg Leu Lys Lys
1               5                   10                  15

Ala

<210> SEQ ID NO 39
<211> LENGTH: 17
<212> TYPE: PRT
<213> ORGANISM: Homo sapiens

<400> SEQUENCE: 39

Arg Lys Glu Trp Leu Thr Asn Phe Met Glu Asp Arg Arg Gln Arg Lys
1               5                   10                  15

Leu

<210> SEQ ID NO 40
<211> LENGTH: 17
<212> TYPE: PRT
<213> ORGANISM: Homo sapiens

<400> SEQUENCE: 40

Lys Lys Gln Thr Thr Leu Ala Phe Lys Pro Ile Lys Lys Gly Lys Lys
1               5                   10                  15

Arg

<210> SEQ ID NO 41
<211> LENGTH: 17
```

```
<212> TYPE: PRT
<213> ORGANISM: Homo sapiens

<400> SEQUENCE: 41

Arg Lys Arg Lys Lys Met Pro Ala Ser Gln Arg Ser Lys Arg Arg Lys
1               5                   10                  15
Thr

<210> SEQ ID NO 42
<211> LENGTH: 23
<212> TYPE: PRT
<213> ORGANISM: Homo sapiens

<400> SEQUENCE: 42

Arg Ala Ile Lys Arg Arg Pro Gly Leu Asp Phe Asp Asp Asp Gly Glu
1               5                   10                  15
Gly Asn Ser Lys Phe Leu Arg
            20

<210> SEQ ID NO 43
<211> LENGTH: 7
<212> TYPE: PRT
<213> ORGANISM: Mus musculus

<400> SEQUENCE: 43

Arg Ile Arg Lys Lys Leu Arg
1               5

<210> SEQ ID NO 44
<211> LENGTH: 18
<212> TYPE: PRT
<213> ORGANISM: Homo sapiens

<400> SEQUENCE: 44

Lys Arg Ala Ala Glu Asp Asp Glu Asp Asp Val Asp Thr Lys Lys
1               5                   10                  15
Gln Lys

<210> SEQ ID NO 45
<211> LENGTH: 8
<212> TYPE: PRT
<213> ORGANISM: Homo sapiens

<400> SEQUENCE: 45

Gly Arg Lys Arg Lys Lys Arg Thr
1               5

<210> SEQ ID NO 46
<211> LENGTH: 13
<212> TYPE: PRT
<213> ORGANISM: Homo sapiens

<400> SEQUENCE: 46

Arg Glu Lys Lys Glu Lys Glu Gln Lys Glu Lys Cys Ala
1               5                   10

<210> SEQ ID NO 47
<211> LENGTH: 13
<212> TYPE: PRT
<213> ORGANISM: Homo sapiens

<400> SEQUENCE: 47

Leu Glu Lys Lys Val Lys Lys Lys Phe Asp Trp Cys Ala
```

```
1               5                    10
```

<210> SEQ ID NO 48
<211> LENGTH: 7
<212> TYPE: PRT
<213> ORGANISM: Arabidopsis sp.

<400> SEQUENCE: 48

```
Arg Lys Arg Arg Thr Lys Lys
1               5
```

<210> SEQ ID NO 49
<211> LENGTH: 13
<212> TYPE: PRT
<213> ORGANISM: Thermoplasma acidophilum

<400> SEQUENCE: 49

```
Ser Asp Lys Lys Val Arg Ser Arg Leu Ile Glu Cys Ala
1               5                    10
```

<210> SEQ ID NO 50
<211> LENGTH: 7
<212> TYPE: PRT
<213> ORGANISM: avian neuroretina

<400> SEQUENCE: 50

```
Leu Lys Arg Lys Leu Gln Arg
1               5
```

<210> SEQ ID NO 51
<211> LENGTH: 7
<212> TYPE: PRT
<213> ORGANISM: Homo sapiens

<400> SEQUENCE: 51

```
Arg Arg Lys Gly Lys Glu Lys
1               5
```

<210> SEQ ID NO 52
<211> LENGTH: 13
<212> TYPE: PRT
<213> ORGANISM: Homo sapiens

<400> SEQUENCE: 52

```
Cys Lys Arg Lys Thr Thr Asn Ala Asp Arg Arg Lys Ala
1               5                    10
```

<210> SEQ ID NO 53
<211> LENGTH: 11
<212> TYPE: PRT
<213> ORGANISM: Homo sapiens

<400> SEQUENCE: 53

```
Val Asn Glu Ala Phe Glu Thr Leu Lys Arg Cys
1               5                    10
```

<210> SEQ ID NO 54
<211> LENGTH: 30
<212> TYPE: PRT
<213> ORGANISM: Zea mays

<400> SEQUENCE: 54

```
Met Pro Thr Glu Glu Arg Val Arg Lys Arg Lys Glu Ser Asn Arg Glu
1               5                    10                   15
```

Ser Ala Arg Arg Ser Arg Tyr Arg Lys Ala Ala His Leu Lys
            20                  25                  30

<210> SEQ ID NO 55
<211> LENGTH: 21
<212> TYPE: PRT
<213> ORGANISM: Rattus sp.

<400> SEQUENCE: 55

Lys Val Asn Ser Arg Lys Arg Arg Lys Glu Val Pro Gly Pro Asn Gly
1               5                   10                  15

Ala Thr Glu Glu Asp
            20

<210> SEQ ID NO 56
<211> LENGTH: 6
<212> TYPE: PRT
<213> ORGANISM: Hepatitis C virus

<400> SEQUENCE: 56

Pro Arg Arg Gly Pro Arg
1               5

<210> SEQ ID NO 57
<211> LENGTH: 14
<212> TYPE: PRT
<213> ORGANISM: Hepatitis C virus

<400> SEQUENCE: 57

Pro Arg Gly Arg Arg Gln Pro Ile Pro Lys Ala Arg Gln Pro
1               5                   10

<210> SEQ ID NO 58
<211> LENGTH: 17
<212> TYPE: PRT
<213> ORGANISM: Homo sapiens

<400> SEQUENCE: 58

Lys Arg Ser Ala Glu Gly Gly Asn Pro Pro Lys Pro Leu Lys Lys Leu
1               5                   10                  15

Arg

<210> SEQ ID NO 59
<211> LENGTH: 11
<212> TYPE: PRT
<213> ORGANISM: Agrobacterium tumefaciens

<400> SEQUENCE: 59

Glu Tyr Leu Ser Arg Lys Gly Lys Leu Gly Leu
1               5                   10

<210> SEQ ID NO 60
<211> LENGTH: 20
<212> TYPE: PRT
<213> ORGANISM: Agrobacterium tumefaciens

<400> SEQUENCE: 60

Pro Lys Arg Pro Arg Asp Arg His Asp Gly Glu Leu Gly Gly Arg Lys
1               5                   10                  15

Arg Ala Arg Gly
            20

<210> SEQ ID NO 61

```
<211> LENGTH: 16
<212> TYPE: PRT
<213> ORGANISM: Xenopus sp.

<400> SEQUENCE: 61

Lys Arg Pro Ala Ala Thr Lys Lys Ala Gly Gln Ala Lys Lys Lys Lys
1               5                   10                  15

<210> SEQ ID NO 62
<211> LENGTH: 18
<212> TYPE: PRT
<213> ORGANISM: Gallus gallus

<400> SEQUENCE: 62

Lys Arg Lys Lys Glu Met Ala Asn Lys Ser Ala Pro Glu Ala Lys Lys
1               5                   10                  15

Lys Lys

<210> SEQ ID NO 63
<211> LENGTH: 15
<212> TYPE: PRT
<213> ORGANISM: Homo sapiens

<400> SEQUENCE: 63

Tyr Asn Asn Gln Ser Ser Asn Phe Gly Pro Met Lys Gly Gly Asn
1               5                   10                  15

<210> SEQ ID NO 64
<211> LENGTH: 9
<212> TYPE: PRT
<213> ORGANISM: Homo sapiens

<400> SEQUENCE: 64

Pro Ala Ala Lys Arg Val Lys Leu Asp
1               5

<210> SEQ ID NO 65
<211> LENGTH: 17
<212> TYPE: PRT
<213> ORGANISM: Homo sapiens

<400> SEQUENCE: 65

Lys Arg Pro Ala Glu Asp Met Glu Glu Glu Gln Ala Phe Lys Arg Ser
1               5                   10                  15

Arg

<210> SEQ ID NO 66
<211> LENGTH: 13
<212> TYPE: PRT
<213> ORGANISM: Saccharomyces cerevisiae

<400> SEQUENCE: 66

Met Asn Lys Ile Pro Ile Lys Asp Leu Leu Asn Pro Gly
1               5                   10

<210> SEQ ID NO 67
<211> LENGTH: 7
<212> TYPE: PRT
<213> ORGANISM: Polyomavirus sp.

<400> SEQUENCE: 67

Pro Lys Lys Ala Arg Glu Asp
1               5
```

```
<210> SEQ ID NO 68
<211> LENGTH: 7
<212> TYPE: PRT
<213> ORGANISM: Polyomavirus sp.

<400> SEQUENCE: 68

Val Ser Arg Lys Arg Pro Arg
1               5

<210> SEQ ID NO 69
<211> LENGTH: 8
<212> TYPE: PRT
<213> ORGANISM: Simian virus 40

<400> SEQUENCE: 69

Ala Pro Thr Lys Arg Lys Gly Ser
1               5

<210> SEQ ID NO 70
<211> LENGTH: 7
<212> TYPE: PRT
<213> ORGANISM: Simian virus 40

<400> SEQUENCE: 70

Pro Asn Lys Lys Lys Arg Lys
1               5

<210> SEQ ID NO 71
<211> LENGTH: 12
<212> TYPE: PRT
<213> ORGANISM: Polyomavirus sp.

<400> SEQUENCE: 71

Glu Glu Asp Gly Pro Gln Lys Lys Lys Arg Arg Leu
1               5                   10

<210> SEQ ID NO 72
<211> LENGTH: 8
<212> TYPE: PRT
<213> ORGANISM: Homo sapiens

<400> SEQUENCE: 72

Pro Leu Leu Lys Lys Ile Lys Gln
1               5

<210> SEQ ID NO 73
<211> LENGTH: 8
<212> TYPE: PRT
<213> ORGANISM: Homo sapiens

<400> SEQUENCE: 73

Pro Pro Gln Lys Lys Ile Lys Ser
1               5

<210> SEQ ID NO 74
<211> LENGTH: 7
<212> TYPE: PRT
<213> ORGANISM: Homo sapiens

<400> SEQUENCE: 74

Pro Gln Pro Lys Lys Lys Pro
1               5

<210> SEQ ID NO 75
```

```
<211> LENGTH: 9
<212> TYPE: PRT
<213> ORGANISM: Homo sapiens

<400> SEQUENCE: 75

Ser Lys Arg Val Ala Lys Arg Lys Leu
1               5

<210> SEQ ID NO 76
<211> LENGTH: 10
<212> TYPE: PRT
<213> ORGANISM: Saccharomyces cerevisiae

<400> SEQUENCE: 76

Ile Lys Tyr Phe Lys Lys Phe Pro Lys Asp
1               5                   10

<210> SEQ ID NO 77
<211> LENGTH: 7
<212> TYPE: PRT
<213> ORGANISM: Saccharomyces cerevisiae

<400> SEQUENCE: 77

Lys Thr Arg Lys His Arg Gly
1               5

<210> SEQ ID NO 78
<211> LENGTH: 7
<212> TYPE: PRT
<213> ORGANISM: Saccharomyces cerevisiae

<400> SEQUENCE: 78

Lys His Arg Lys His Pro Gly
1               5

<210> SEQ ID NO 79
<211> LENGTH: 8
<212> TYPE: PRT
<213> ORGANISM: Homo sapiens

<400> SEQUENCE: 79

Pro Gln Ser Arg Lys Lys Leu Arg
1               5

<210> SEQ ID NO 80
<211> LENGTH: 9
<212> TYPE: PRT
<213> ORGANISM: Homo sapiens

<400> SEQUENCE: 80

Lys Lys Glu Lys Lys Lys Ser Lys Lys
1               5

<210> SEQ ID NO 81
<211> LENGTH: 9
<212> TYPE: PRT
<213> ORGANISM: Human immunodeficiency virus

<400> SEQUENCE: 81

Leu Pro Pro Leu Glu Arg Leu Thr Leu
1               5

<210> SEQ ID NO 82
<211> LENGTH: 10
<212> TYPE: PRT
```

<213> ORGANISM: Mus musculus

<400> SEQUENCE: 82

Leu Ala Leu Lys Leu Ala Gly Leu Asp Ile
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 83

Arg Lys Lys Lys Arg Lys Val
1               5

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 84

Pro Lys Lys Lys Arg Lys Val Leu Pro Pro Leu Glu Arg Leu Thr Leu
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 85

Leu Pro Pro Leu Glu Arg Leu Thr Leu Pro Lys Lys Lys Arg Lys Val
1               5                   10                  15

<210> SEQ ID NO 86
<211> LENGTH: 22
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 86

Arg Gln Ala Arg Arg Asn Arg Arg Arg Trp Arg Leu Pro Pro Leu
1               5                   10                  15

Glu Arg Leu Thr Leu Asp
            20

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 87

Pro Lys Lys Lys Arg Lys Val Leu Pro Pro Leu Glu Arg Leu Thr Leu
1               5                   10                  15

```
Pro Lys Lys Lys Arg Lys Val
            20

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 88

Arg Lys Lys Lys Arg Lys Val Leu Pro Pro Leu Glu Arg Leu Thr Leu
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 89

Leu Pro Pro Leu Glu Arg Leu Thr Leu Arg Lys Lys Lys Arg Lys Val
1               5                   10                  15

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 90

Arg Lys Lys Lys Arg Lys Val Leu Ala Leu Lys Leu Ala Gly Leu Asp
1               5                   10                  15

Ile

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 91

Leu Ala Leu Lys Leu Ala Gly Leu Asp Ile Arg Lys Lys Lys Arg Lys
1               5                   10                  15

Val

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 92

Pro Lys Lys Lys Arg Lys Val Pro Lys Lys Lys Arg Lys Val
1               5                   10
```

```
<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 93

Arg Ile Arg Lys Lys Leu Arg Arg Ile Arg Lys Lys Leu Arg
1               5                   10

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 94

Arg Lys Lys Arg Arg Gln Arg Arg Arg Lys Lys Arg Arg Gln Arg
1               5                   10                  15

Arg Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 95

Pro Arg Arg Arg Lys Pro Arg Arg Arg Lys
1               5                   10

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 96

Pro Pro Arg Lys Lys Arg Thr Val Val Pro Pro Arg Lys Lys Arg Thr
1               5                   10                  15

Val Val

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 97

Pro Lys Lys Lys Arg Lys Val Pro Pro Arg Lys Lys Arg Thr Val Val
1               5                   10                  15

<210> SEQ ID NO 98
<211> LENGTH: 14
<212> TYPE: PRT
<213> ORGANISM: Artificial Sequence
<220> FEATURE:
```

```
<223> OTHER INFORMATION: Description of Artificial Sequence: Designed
      antimicrobial polypeptide

<400> SEQUENCE: 98

Arg Lys Lys Lys Arg Lys Val Arg Lys Lys Arg Lys Val
1               5                   10

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 99

Arg Lys Lys Lys Arg Lys Val Arg Lys Lys Arg Lys Val Arg Lys
1               5                   10                  15

Lys Lys Arg Lys Val
            20

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 100

Arg Lys Lys Lys Arg Lys Val Arg Lys Lys Arg Lys Val Arg Lys
1               5                   10                  15

Lys Lys Arg Lys Val Arg Lys Lys Lys Arg Lys Val
            20                  25

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Designed
      antimicrobial polypeptide containing a terminal amide group

<400> SEQUENCE: 101

Pro Arg Arg Arg Lys
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Designed
      antimicrobial polypeptide containing a terminal amide group

<400> SEQUENCE: 102

Arg Lys Lys Lys Arg Lys Val
1               5

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Designed
      antimicrobial polypeptide containing a terminal amide group
```

```
<400> SEQUENCE: 103

Arg Lys Lys Lys Arg Lys Val Arg Lys Lys Arg Lys Val
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 104

Pro Lys Lys Lys Arg Arg Val
1               5

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 105

Arg Lys Lys Lys Arg Lys Val Val Lys Arg Lys Lys Lys Arg
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 106

Arg Lys Lys Lys Arg Lys Val Lys Arg Lys Lys Lys Arg
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 107

Leu Lys Arg Lys Leu Gln Arg Leu Lys Arg Lys Leu Gln Arg
1               5                   10

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 108

Pro Lys Lys Lys Arg Lys Val Ala Leu Gly Lys Leu Ala Leu Gly Lys
1               5                   10                  15

Leu

<210> SEQ ID NO 109
```

```
<211> LENGTH: 17
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 109

Arg Gln Ala Arg Arg Asn Arg Arg Arg Trp Arg Ile Ala Gly Lys
1               5                   10                  15

Ile

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Designed
      antimicrobial polypeptide

<400> SEQUENCE: 110

Met Arg Lys Lys Lys Arg Lys Val Arg Lys Lys Lys Arg Lys Val
1               5                   10                  15

<210> SEQ ID NO 111
<211> LENGTH: 139
<212> TYPE: DNA
<213> ORGANISM: Artificial Sequence
<220> FEATURE:
<223> OTHER INFORMATION: Description of Artificial Sequence: Synthetic
      DNA encoding a designed antimicrobial polypeptide sequence
<220> FEATURE:
<221> NAME/KEY: CDS
<222> LOCATION: (86)..(130)

<400> SEQUENCE: 111
gaaattaata cgactcacta tagggagacc acaacggttt ccctctagaa ataattttgt      60
ttaactttaa gaaggagata tacat atg cgc att cgc aaa aaa ctc cgc cgt      112
                             Met Arg Ile Arg Lys Lys Leu Arg Arg
                             1               5 atc cgt aag aaa ctc cgc taatgaata                                      139
Ile Arg Lys Lys Leu Arg
10              15

<210> SEQ ID NO 112
<211> LENGTH: 15
<212> TYPE: PRT
<213> ORGANISM: Artificial Sequence
<220> FEATURE:
<223> OTHER INFORMATION: Synthetic Construct

<400> SEQUENCE: 112

Met Arg Ile Arg Lys Lys Leu Arg Arg Ile Arg Lys Lys Leu Arg
1               5                   10                  15

<210> SEQ ID NO 113
<211> LENGTH: 160
<212> TYPE: DNA
<213> ORGANISM: Artificial Sequence
<220> FEATURE:
<223> OTHER INFORMATION: Description of Artificial Sequence: Synthetic
      DNA encoding a designed antimicrobial polypeptide sequence
<220> FEATURE:
<221> NAME/KEY: CDS
<222> LOCATION: (86)..(151)

<400> SEQUENCE: 113
```

```
gaaattaata cgactcacta tagggagacc acaacggttt ccctctagaa ataattttgt     60
ttaactttaa gaaggagata tacat atg cgc caa gct cgt cgt aat cgt cgc     112
                           Met Arg Gln Ala Arg Arg Asn Arg Arg
                            1               5 cgt cgc tgg cgt ctg cca ccg ctc gaa cgc ttg acc ttg taatgaata       160
Arg Arg Trp Arg Leu Pro Pro Leu Glu Arg Leu Thr Leu
 10              15                  20
```

<210> SEQ ID NO 114
<211> LENGTH: 22
<212> TYPE: PRT
<213> ORGANISM: Artificial Sequence
<220> FEATURE:
<223> OTHER INFORMATION: Synthetic Construct

<400> SEQUENCE: 114

```
Met Arg Gln Ala Arg Arg Asn Arg Arg Arg Trp Arg Leu Pro Pro
 1               5                  10                  15

Leu Glu Arg Leu Thr Leu
             20
```

<210> SEQ ID NO 115
<211> LENGTH: 166
<212> TYPE: DNA
<213> ORGANISM: Artificial Sequence
<220> FEATURE:
<223> OTHER INFORMATION: Description of Artificial Sequence: Synthetic
      DNA encoding a designed antimicrobial polypeptide sequence
<220> FEATURE:
<221> NAME/KEY: CDS
<222> LOCATION: (86)..(157)

<400> SEQUENCE: 115

```
gaaattaata cgactcacta tagggagacc acaacggttt ccctctagaa ataattttgt     60
ttaactttaa gaaggagata tacat atg cct aag aag aaa cgt aag gtc tta     112
                           Met Pro Lys Lys Lys Arg Lys Val Leu
                            1               5 ccg cca tta gaa cgt ctg act tta ccg aaa aag aag cgc aaa gtt         157
Pro Pro Leu Glu Arg Leu Thr Leu Pro Lys Lys Lys Arg Lys Val
 10              15                  20 taatgaata                                                            166
```

<210> SEQ ID NO 116
<211> LENGTH: 24
<212> TYPE: PRT
<213> ORGANISM: Artificial Sequence
<220> FEATURE:
<223> OTHER INFORMATION: Synthetic Construct

<400> SEQUENCE: 116

```
Met Pro Lys Lys Lys Arg Lys Val Leu Pro Pro Leu Glu Arg Leu Thr
 1               5                  10                  15

Leu Pro Lys Lys Lys Arg Lys Val
             20
```

<210> SEQ ID NO 117
<211> LENGTH: 85
<212> TYPE: DNA
<213> ORGANISM: Artificial Sequence
<220> FEATURE:
<223> OTHER INFORMATION: Description of Artificial Sequence: Synthetic
      DNA used as a primer

<400> SEQUENCE: 117

```
gaaattaata cgactcacta tagggagacc acaacggttt ccctctagaa ataattttgt      60 ttaacttta gaaggagata tacat                                              85
```

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA used as a primer

<400> SEQUENCE: 118

```
tattcattag cggagtttct tacgg                                             25
```

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA used as a primer

<400> SEQUENCE: 119

```
tattcattac aaggtcaagc gttcg                                             25
```

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA used as a primer

<400> SEQUENCE: 120

```
tattcattaa actttgcgct tcttt                                             25
```

<210> SEQ ID NO 121
<211> LENGTH: 81
<212> TYPE: DNA
<213> ORGANISM: Artificial Sequence
<220> FEATURE:
<223> OTHER INFORMATION: Description of Artificial Sequence: Synthetic
      DNA encoding a designed antimicrobial polypeptide sequence
<220> FEATURE:
<221> NAME/KEY: CDS
<222> LOCATION: (7)..(72)

<400> SEQUENCE: 121

```
gaattc atg cat cac cat cac cat cac gaa cgt ata cgt aaa aag ctg          48
       Met His His His His His His Glu Arg Ile Arg Lys Lys Leu
       1               5                   10 cgt cgc atc cgt aaa aag ctg cgt taactgcag                               81
Arg Arg Ile Arg Lys Lys Leu Arg
15                  20
```

<210> SEQ ID NO 122
<211> LENGTH: 22
<212> TYPE: PRT
<213> ORGANISM: Artificial Sequence
<220> FEATURE:
<223> OTHER INFORMATION: Synthetic Construct

<400> SEQUENCE: 122

```
Met His His His His His His Glu Arg Ile Arg Lys Lys Leu Arg Arg
1               5                   10                  15

Ile Arg Lys Lys Leu Arg
```

```
<210> SEQ ID NO 123
<211> LENGTH: 81
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 123
ctgcagttaa cgcagctttt tacggatgcg acgcagcttt ttacgtatac gttcgtgatg      60
gtgatggtga tgcatgaatt c                                                81
```

ANTIMICROBIAL POLYPEPTIDE AND UTILIZATION THEREOF

TECHNICAL FIELD

The present invention relates to antimicrobial polypeptide comprising independent peptide chains in the form that does not naturally occur and an antimicrobial agent (pharmaceutical composition) having the polypeptide as the main component.

BACKGROUND ART

It is believed that antimicrobial polypeptide has a broad antimicrobial spectrum so that drug resistant bacterium hardly appears, and therefore antimicrobial polypeptide is expected to be used for the purpose of preventing and treating bacterial infectious diseases of human beings and animals or providing antimicrobial properties to products such as food. A large number of antimicrobial polypeptides have been isolated from animals and plants by now.

For example, Japanese Laid-Open Patent Publication No. 2000-63400 discloses antimicrobial polypeptide derived from Taiwan beetle and an antimicrobial agent having the antimicrobial polypeptide as an effective component. Japanese Laid-Open Patent Publication No. 2001-186887 discloses antimicrobial polypeptide derived from scorpion poison and an antimicrobial agent having the antimicrobial polypeptide as an effective component. Furthermore, International Publication No. WO98/51794 discloses antimicrobial polypeptide derived from human, which is a member of the defensin super family, and an antimicrobial agent having the antimicrobial polypeptide as an effective component. International Publication No. WO99/26971 discloses antimicrobial polypeptide derived from casein and an antimicrobial agent (more specifically, oral composition such as dentifrices or mouth washing liquid) having the antimicrobial polypeptide as an effective component. International Publication No. WO00/09553 discloses antimicrobial polypeptide derived from a ranid. International Publication No. WO01/009175 discloses a modified cysteine-containing antimicrobial polypeptide derived from plant defensin.

All of the antimicrobial polypeptides disclosed in the above-described publications are obtained by isolating antimicrobial polypeptides that are originally present as an antimicrobial polypeptide in nature and are discovered (or polypeptide obtained by partially modifying the amino acid sequence of a native antimicrobial polypeptide). Therefore, as long as peptide present inherently as an antimicrobial polypeptide is used as the main component, it is difficult to develop an antimicrobial agent having better antibacterial activity or antibacterial spectrum than the polypeptide originally had in nature.

DISCLOSURE OF INVENTION

The antimicrobial polypeptide disclosed herein is a polypeptide developed by an approach different from a conventionally known antimicrobial polypeptide. That is, the present invention provides an artificially synthesized antimicrobial polypeptide that does not naturally occur that was created by utilizing the amino acid sequence contained in a peptide different from a peptide occurring in nature as antimicrobial polypeptide. Furthermore, the present invention provides a method for producing an antimicrobial polypeptide disclosed herein. The present invention further provides a polynucleotide sequence encoding the antimicrobial polypeptide disclosed herein and an artificially synthesized polynucleotide that does not naturally occur containing this sequence (typically, consisting of this sequence). Moreover, the present invention provides an antimicrobial agent (pharmaceutical composition) having such an antimicrobial polypeptide or a polynucleotide encoding the polypeptide as the main component.

The antimicrobial polypeptide disclosed herein contains one or two or more units of nuclear localization signal sequence (hereinafter, referred to as NLS) of one or two or more kinds and/or partially modified sequence of the NLS in its peptide chain. Typically, the total number of amino acid residues contained in the one or two or more units of NLS and/or modified sequence of the NLS (i.e., amino acid residues constituting that sequence) is at least 5 and amounts to 30% or more (preferably 40% or more) of the total number of amino acid residues constituting the peptide chain.

The NLS is a nuclear localization signal sequence that is isolated from various organism species or virus, and inherently is a partial sequence present in various polypeptides that transfer to the nucleus in a cell. However, the inventors of the present invention found out that NLS in an independent form itself has antimicrobial properties with respect to bacteria or the like and achieved the present invention.

The antimicrobial polypeptide of the present invention can exhibit high antimicrobial activities by including NLS as a main element. In particular, the present invention can have a board antimicrobial spectrum with respect to gram-negative bacteria and gram-positive bacteria.

In the antimicrobial polypeptide of the present invention, preferably the total number of amino acid residues constituting the peptide chain is 5 or more and 100 or less. A polypeptide with such a length can exhibit high antimicrobial activities stably. Since the peptide chain is relatively short, synthesis is easy and economical. A peptide in which the total number of amino acid residues contained in the NLS and/or the modified sequence of the NLS amounts to 90% or more (e.g., 100%) of the total number of amino acid residues constituting the peptide chain is most preferable. Such a peptide based on NLS can have particularly high antimicrobial activities.

Furthermore, it is preferable that 40% or more of the total number of amino acid residues constituting the peptide chain are basic amino acid residues (typically arginine and lysine). When the ratio of the number of basic amino acid residues present is high, higher antimicrobial activities can be obtained.

One preferable antimicrobial polypeptide is characterized in that the NLS and/or the modified sequence of the NLS is arranged such that two or more units thereof are in proximity to each other. When two or more units of NLS are present in one peptide chain, the antimicrobial activities are improved. It is particularly preferable that the units are adjacent in tandem.

Another preferable antimicrobial polypeptide provided by the present invention may comprise another sequence that can enhance the antimicrobial activities of NLS. Regarding this, the inventors of the present invention found out that a sequence conventionally known as nuclear export signal sequence (hereinafter referred to as NES) can contribute to increasing the antimicrobial activities of the peptide. Therefore, the present invention provides an antimicrobial polypeptide further comprising at least one unit of NES or partially modified sequence of the NES in the peptide chain, in addition to the NLS and/or a modified sequence of NLS.

A preferable polypeptide in this form is characterized in that at least one unit of the NES or the modified sequence of the NES is arranged in proximity to an N-terminal side or a C-terminal side of the NLS or the modified sequence of the NLS. The polypeptide (peptide chain) in which NES (or a modified sequence thereof) and NLS (or a modified sequence thereof) are adjacent to each other can exhibit high antimicrobial activities with respect to bacteria, in particular, gram-positive bacteria such as yellow staphylococcus.

The present invention provides an antimicrobial agent (i.e., a pharmaceutical composition) comprising the antimicrobial polypeptide disclosed herein as the main component. Typically, the antimicrobial agent can contain pharmaceutically acceptable carriers of various kinds (secondary component), in addition to the antimicrobial polypeptide of the present invention that is the main component, depending on the use.

The present invention also provides a nucleotide sequence encoding the antimicrobial polypeptide disclosed herein and a nucleotide sequence complementary to the sequence. Furthermore, the present invention provides an artificially synthesized polynucleotide (which can be in the form of a DNA segment or a RNA segment) that does not naturally occur, and includes these nucleotide sequences or consists substantially of these sequences.

The present invention also provides a method for preferably producing the antimicrobial polypeptide disclosed herein. Typically, the method disclosed herein includes selecting at least one amino acid sequence comprising 5 or more amino acid residues known as a nuclear localization signal sequence (NLS); designing a peptide chain such that one or two or more units of the selected NLS and/or partially modified sequence of the NLS is contained, and the total number of amino acid residues contained in the one or two or more units of NLS and/or the modified sequence of the NLS amounts to 30% or more (preferable 40% or more) of the total number of amino acid residues; and synthesizing an antimicrobial polypeptide having the designed peptide chain.

A preferable method for partially modifying the NLS, the following can be used:(a) deleting at least one non-basic amino acid residue of a native NLS; (b) adding at least one basic amino acid residue to a native NLS; and (c) substituting at least one non-basic amino acid residue contained in a native NLS with a basic amino acid residue.

Sequence listing free text

Figure 1:
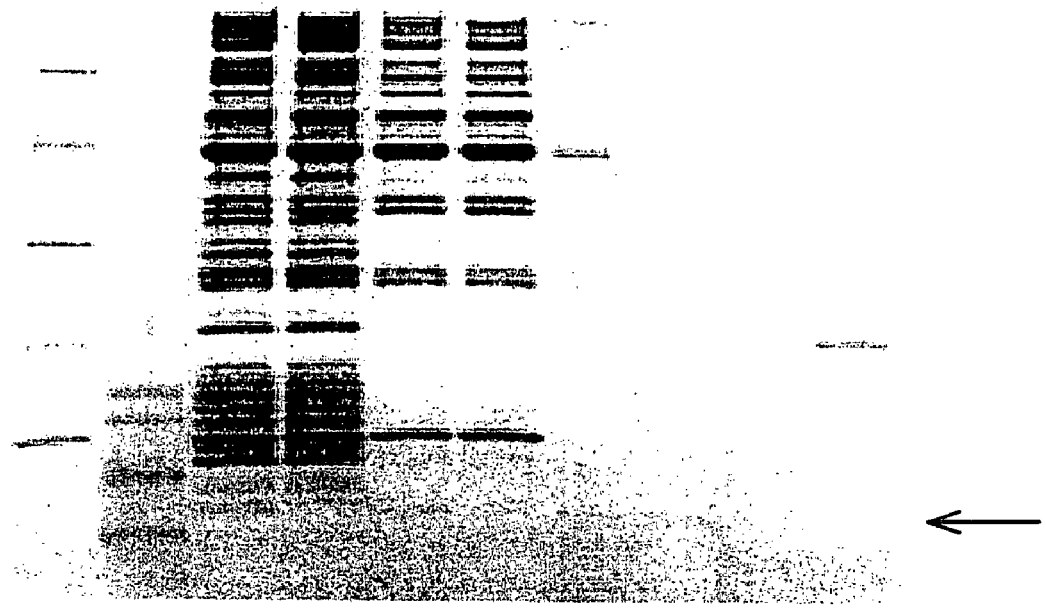
FIG. 1 is a photograph showing the results of fractionating a sample containing polypeptide that is synthesized by a cell-free protein synthetic system by polyacrylamide gel electrophoresis.

| | |
|---|---|
| Sequence No. 83 | designed antimicrobial polypeptide |
| Sequence No. 84 | designed antimicrobial polypeptide |
| Sequence No. 85 | designed antimicrobial polypeptide |
| Sequence No. 86 | designed antimicrobial polypeptide |
| Sequence No. 87 | designed antimicrobial polypeptide |
| Sequence No. 88 | designed antimicrobial polypeptide |
| Sequence No. 89 | designed antimicrobial polypeptide |
| Sequence No. 90 | designed antimicrobial polypeptide |
| Sequence No. 91 | designed antimicrobial polypeptide |
| Sequence No. 92 | designed antimicrobial polypeptide |
| Sequence No. 93 | designed antimicrobial polypeptide |
| Sequence No. 94 | designed antimicrobial polypeptide |
| Sequence No. 95 | designed antimicrobial polypeptide |
| Sequence No. 96 | designed antimicrobial polypeptide |
| Sequence No. 97 | designed antimicrobial polypeptide |
| Sequence No. 98 | designed antimicrobial polypeptide |
| Sequence No. 99 | designed antimicrobial polypeptide |
| Sequence No. 100 | designed antimicrobial polypeptide |
| Sequence No. 101 | designed antimicrobial polypeptide containing a terminal amide group |
| Sequence No. 102 | designed antimicrobial polypeptide containing a terminal amide group |
| Sequence No. 103 | designed antimicrobial polypeptide containing a terminal amide group |
| Sequence No. 104 | designed antimicrobial polypeptide |
| Sequence No. 105 | designed antimicrobial polypeptide |
| Sequence No. 106 | designed antimicrobial polypeptide |
| Sequence No. 107 | designed antimicrobial polypeptide |
| Sequence No. 108 | designed antimicrobial polypeptide |
| Sequence No. 109 | designed antimicrobial polypeptide |
| Sequence No. 110 | designed antimicrobial polypeptide |
| Sequence No. 111 | synthetic DNA encoding a designed antimicrobial polypeptide sequence |
| Sequence No. 112 | designed antimicrobial polypeptide |
| Sequence No. 113 | synthetic DNA encoding a designed antimicrobial polypeptide sequence |
| Sequence No. 114 | designed antimicrobial polypeptide |
| Sequence No. 115 | synthetic DNA encoding a designed antimicrobial polypeptide sequence |
| Sequence No. 116 | designed antimicrobial polypeptide |
| Sequence No. 117 | synthetic DNA used as a primer |
| Sequence No. 118 | synthetic DNA used as a primer |
| Sequence No. 119 | synthetic DNA used as a primer |
| Sequence No. 120 | synthetic DNA used as a primer |
| Sequence No. 121 | synthetic DNA encoding a designed antimicrobial polypeptide sequence |
| Sequence No. 122 | designed antimicrobial polypeptide |
| Sequence No. 123 | synthetic DNA |

Best Mode for Carrying Out the Invention

In this specification, "artificially synthesized antimicrobial polypeptide or polynucleotide that does not naturally occur" refers to antimicrobial polypeptide or polynucleotide whose peptide chain or nucleotide chain (total length) does not occur in nature, but is artificially chemically synthesized or biosynthesized (i.e., produced based on genetic engineering).

"Polypeptide" refers to an amino acid polymer having a plurality of peptide bonds, and is not limited by the number of the amino acid residues contained in the peptide chain. The polypeptide in this specification includes so-called oligopeptides, which have less than 10 amino acid residues (e.g., the total number of amino acid residues is 5 to 7).

"Polynucleotide" is a general term referring to polymer (nucleic acid) in which a plurality of nucleotides are bonded by phosphodiester bonds, and is not limited by the number of the nucleotides. The polynucleotide includes DNA fragments and RNA fragments having various lengths.

"Amino acid residue" is a term encompassing N-terminal amino acid and C-terminal amino acid of peptide chain, unless otherwise specified.

In this specification, "NLS" or "nuclear localization signal sequences" is not limited to a specific amino acid sequence and refers to general amino acid sequences that are known as a nuclear localization signal sequence, unless otherwise specified. Typical examples of amino acid sequences that are known as NLS are listed in the column of the sequence listing (Sequence Nos. 1 to 80), which are not particularly intended to limit the present invention.

In this specification, "NES" or "nuclear export signal sequence" is not limited to a specific amino acid sequence and refers to general amino acid sequences that are known as a nuclear export signal sequence, unless otherwise specified. Typical examples of amino acid sequences that are known as NES are listed in the column of the sequence listing (Sequence Nos. 81, 82), which are not particularly intended to limit the present invention.

Regarding the antimicrobial polypeptide containing NLS or NES, "antimicrobial polypeptide containing a partially modified sequence of NLS (or NES)" refers to antimicrobial polypeptide containing a sequence in which one to several amino acid residues of NLS (or NES) are modified (e.g., a sequence in which the carboxyl group of C-terminal amino acid is amidated), or a modified NLS (or NES) that is formed by substituting, deleting, and/or adding one to several amino acid residues in the NLS (or NES), so as to be as antimicrobial as or more antimicrobial than polypeptide containing the predetermined NLS (or NES). For example, (i) a modified sequence that occurs by so-called conservative amino acid substitutions in which about 1 to 5 amino acid residues of a predetermined NLS are conservatively substituted (e.g., a sequence in which 1, 2 or 3 basic amino acid residues are substituted with other basic amino acid residues) that are different from each other, (ii) a modified sequence in which about 1 to 3 amino acid residues (preferably basic amino acid residues) are added to a predetermined NLS, (iii) a modified sequence in which about 1 to 3 amino acid residues (preferably non-basic amino acid residues) are deleted from a predetermined NLS, and (iv) a modified sequence in which a methionine residue (including the case where an amino group is formylated) is added to an amino terminal of a native NLS are typical examples that are included in "antimicrobial polypeptide containing a partially modified sequence" in this specification.

Regarding NLS and NES, "one unit" refers to one sequence constituting NLS or NES. Therefore, the case where 2 units of NLS are contained in a peptide chain means that two sequences that are independently regarded as NLS (or NES), regardless of whether they are the same type or different types are present in the peptide chain.

Hereinafter, preferred embodiments of the present invention will be described. The matters that are other than those particularly mentioned in this specification (e.g., primary structure or chain length of an antimicrobial polypeptide) and that are necessary to carry out the present invention (e.g., general matters involved in, for example, peptide synthesis, polynucleotide synthesis, or preparation of a pharmaceutical including peptide as a component) can be considered to be a matter of design of those skilled in the art based on the prior art in the fields of organic chemistry, biochemistry, genetic engineering, protein engineering, molecular biology, pharmaceuticals, medicine or the like. The present invention can be carried out based on the contents disclosed in this specification and the common general technical knowledge in the field. All the contents of the patent documents, the patent application documents and other publications cited in this specification are incorporated in this specification by reference.

In the following description, the amino acid residues constituting a peptide chain are expressed by one letter representation (however, three letter representation in the sequence list) according to the nomenclature for amino acids shown in the IUPAC-IUB guideline. Furthermore, the representation "NLS" includes "the partially modified sequence" (that is, modified NLS sequence) based on the above definition, unless otherwise specified. The same applies for the case of NES.

The antimicrobial polypeptide provided by the present invention is polypeptide that does not naturally exist but artificially synthesized and has a primary structure to which NLS is incorporated or that consists only of NLS. In other words, the ratio of NLS in the entire amino acid sequence is significantly large, compared with a native nuclear localization polypeptide (peptide chain) in which NLS is contained in one portion. Typically, the total number of the amino acid residues contained in NLS is at least 5 amino acids (preferably 7 or more amino acids), the number of these amino acid residues accounts for as much as 30% or more (preferably 40% or more) of the total number of the amino acid residues constituting the total length of the peptide chain. Furthermore, it is preferable that at least 70% of the total number of the amino acid residues constituting the peptide chain are contained in the NLS portion, and it is most preferable that at least 90% of the total number of the amino acid residues are contained in the NLS portion.

In the antimicrobial peptide of the present invention, it is preferable that all the amino acid residues are L-amino acids, but a part or all of the amino acid residues may be substituted with D-amino acids, as long as the antimicrobial activity is not lost. For example, in the case where polypeptide constituted by the amino acid sequences disclosed herein is to be chemically synthesized, a part or all thereof can be constituted by D-amino acid residues. The chain length (in other words, the number of amino acid residues) of the polypeptide can differ with the length of the contained NLS or NES, and therefore there is no particular limitation, but it is preferable that the polypeptide is constituted by about 5 to 100 amino acid residues, more preferably about 7 to 50 amino acid residues, and most preferably about 9 to 30 amino acid residues (see Table 1).

There is no particular limitation regarding the conformation of the polypeptide, as long as the polypeptide is antimicrobial in the environment in which it is used, but linear or helical polypeptide is preferable because this hardly becomes an immunogen (antigen). The polypeptide having such a shape hardly constitutes epitope. From this viewpoint, for the polypeptide applied to an antimicrobial agent, a linear polypeptide having a relatively low molecular weight (typically the total number of the amino acid residues: 5 to 30, preferably the total number of the amino acid residues: 5 to 20) is preferable. An amino acid sequence in which no cysteine residue is contained or the ratio of the cysteine residues present is small is preferable.

As the NLS for constituting the polypeptide of the present invention, any one of known native NLSs that are discovered from various organisms or viruses is selected and can be utilized with its sequence held. Specific examples include NLSs shown in Sequence Nos. 1 to 80. NLSs that have a high content of basic amino acid residues are preferable. For example, NLSs in which at least 40% (preferably at least 50%) of amino acid residues are basic amino acid residues (lysine and/or arginine) are preferable. Polypeptides containing one kind or two or more kinds of these NLSs are preferable.

However, it is designed that at least five amino acid residues that accounts for at least 40% of the total number of amino acid residues constituting a peptide chain belong to the NLS portion. NLSs in which about 5 to 25 amino acid residues constitute one unit are preferable. For example, polypeptides containing one unit or two or more units of the NLS constituted by at least 5 amino acid residues such as RRMKWKK (Sequence No. 1), RVHPYQR (Sequence No. 2), PKKKRKV (Sequence No. 4), GKKRSKA (Sequence No. 5), RGRRRRQR (Sequence No. 7), RKKRRQRRR (Sequence No. 20), and PRRRK (Sequence No. 26) (typically the total number of amino acid residues is 5 to 100) are preferable. Polypeptides that consist of one unit of such an NLS may be used.

On the other hand, the polypeptide of the present invention is not constituted by only one unit of NLS that has four or less amino acid residues in one unit such as RKRR (Sequence No. 27). In this case, an amino acid sequence is designed so as to have five or more amino acid residues in total by combining the NLS with the same or a different type of NLS. In other words, an amino acid sequence containing two or more units (typically, two, three or four units) of NLS that have four or less amino acid residues in one unit can be designed. For example, when RKRR (Sequence No. 27) is selected as the NLS, a sequence consisting of 8 amino acid residues (RKRRRKRR) in which two units of that sequence are linked in tandem can be designed.

It is preferable to select NLS rich with basic amino acid residues when selecting NLS to construct an antimicrobial polypeptide from an available information resource such as database. For example, NLS in which arginine residues and/or lysine residues account for 40% or more, preferably 50% or more, and most preferably 70% or more of the total number of the amino acid residues can be used.

When designing an amino acid sequence so as to contain two or three or more units of NLS, it is preferable to design an amino acid sequence such that these NLSs are arranged adjacent to each other in a peptide chain. In this case, it is preferable that the C-terminal amino acid of one of the adjacent NLSs is bonded directly to the N-terminal amino acid of the other NLS (which the examples that will described later). However, one to several amino acid residues may be present as a linker between the two adjacent NLSs.

The antimicrobial polypeptide of the present invention may be such that the entire amino acid sequence is constituted only by NLSs of one or two or more kinds, but amino acid residues (amino acid sequences) that are not contained in the NLS can be contained, as long as antimicrobial properties can be maintained. A sequence that can maintain the linear shape of the peptide chain is preferable as a sequence of a portion other than the NLS, but the present invention is not limited thereto.

Furthermore, it is preferable to design an amino acid sequence so as to contain another sequence that has an effect of enhancing the antimicrobial activity of the internal NLS. As described above, NES can be a choice as a preferable sequence for this purpose.

LPPLERLTL (Sequence No. 81) and LALKLAGLDI (Sequence No. 82) can be used as typical NES sequences. Polypeptide having high antimicrobial activity can be constructed by combining the NLS with various NESs whose amino acid sequence is already known. Preferably, a peptide chain is constructed such that NES is adjacent to the N-terminal side or the C-terminal side of the NLS. As a polypeptide of this form, for example, the following polypeptides can be used: a polypeptide in which NLS and NES are arranged in tandem in this order from the N-terminal side, a polypeptide in which NES and NLS are arranged in tandem in this order from the N-terminal side, or a polypeptide in which NLS, NES and NLS are arranged in tandem in this order from the N-terminal side (in this case, with NES sandwiched, the NLS on the N-terminal side and the NLS on the C-terminal side can be the same type or different types).

As the NLS or NES constituting the antimicrobial polypeptide of the present invention, not only a native type sequence, but also various partially modified sequences can be used, as long as the antimicrobial activities are not impaired. In other words, a polypeptide exhibiting higher antimicrobial activities can be obtained by designing an amino acid sequence (peptide chain) containing an appropriately modified sequence of a native NLS.

Typical modifications of this kind are as follows: One to three amino acid residues in the sequence are substituted conservatively; and a methionine residue is added to the N-terminal of a peptide chain (NLS) (which is preferable to synthesize biologically a designed peptide chain using a recombinant DNA technology). Other preferable modification for enhancing the antimicrobial activity is as follows: At least one non-basic amino acid residue (neutral or acidic amino acid residue) of a native NLS is deleted; at least one basic amino acid (typically arginine or lysine) is added to a native NLS; and at least one non-basic amino acid residue contained in a native NLS is substituted with a basic amino acid residue. Furthermore, amidating a carboxyl group of a C-terminal amino acid of a peptide chain or acylating (typically acetylating) the amino group at the N-terminal is a preferable modification.

For example, a polypeptide having one or two or more units of sequence RKKKRKV (Sequence No.83) in which proline of PKKKRKV (Sequence No. 4), which is a typical NLS consisting of 7 amino acid residues, is substituted with a basic amino acid residue is one of the novel antimicrobial polypeptides provided by the present invention.

A polypeptide constituted by such a modified sequence and further modified such that the carboxyl group at its C-terminal is amidated, such as RKKKRKV-CONH$_2$ (Sequence No. 102) or RKKKRKVRKKKRKV-CONH$_2$ (Sequence No. 103) is a preferable novel antimicrobial polypeptide provided by the present invention.

Specific examples of the novel amino acid sequence (designed peptide chain) provided by the present invention include amino acid sequences shown in Sequence Nos. 83, 84, 85, 86, 87, 88, 89, 90, 91, 92, 93, 94, 95, 96, 97, 98, 99, 100, 101, 102, 103, 104, 105, 106, 107, 108, 109, 110, 112, 114 and 116 (or modified sequences obtained by substituting (conservative substitution or the like), deleting and/or adding one or two or several amino acid residues of those amino acid sequences). The polypeptides constituted substantially by these amino acid sequences have high antimicrobial activity against gram-positive bacteria and gram-negative bacteria (see the examples described later).

All of these polypeptides are constituted by 30 or less amino acid residues (more specifically, 5 to 28 amino acid residues), and are preferable in order to maintain the linear shape. Furthermore, these polypeptides have low immunogenicity, so that these polypeptides are preferable as the main component (antimicrobial component) of an antimicrobial agent.

Furthermore, polypeptides that do not naturally occur and are artificially synthesized (which, however, have 100 or less amino acid residues in total, preferably 50 or less amino acid residues in total) containing one or two or more kinds of the amino acid sequences shown in Sequence Nos. 83, 84, 85, 86, 87, 88, 89, 90, 91, 92, 93, 94, 95, 96, 97, 98, 99, 100, 101, 102, 103, 104, 105, 106, 107, 108, 109, 110, 112, 114 and 116 (or modified sequences obtained by substituting (conservative substitution or the like), deleting and/or adding one or two or several amino acid residues of those amino acid sequences) are provided by the present invention.

Once an amino acid sequence is designed as described above, then a peptide chain (i.e., the antimicrobial polypeptide of the present invention) can be synthesized in conventionally known various methods according to the amino acid sequence. An antimicrobial polypeptide can be produced easily, for example, according to a general chemosynthetic method. Either a conventionally known solid-phase synthetic method or liquid-phase synthetic method can be used. A solid-phase synthetic method using Boc (t-butyloxycarbonyl) or Fmoc (9-fluorenylmethoxycarbonyl) as a protective group for the amino group is preferable.

For the antimicrobial polypeptide of the present invention, a peptide chain having a desired amino acid sequence and a modified (e.g., C-terminal amidated) portion can be easily synthesized by a solid-phase synthetic method using a commercially available peptide synthesis apparatus (available from PerSeptive Biosystem, Applied Biosystems or the like).

Alternatively, the antimicrobial peptide of the present invention may be synthesized biologically based on a genetic engineering approach. This approach is preferable to produce a polypeptide having a relatively long chain. In other words, DNA (structural gene) is synthesized so as to contain a nucleotide sequence (typically including ATG start codon) determined so as to encode a desired antimicrobial polypeptide (amino acid sequence designed based on NLS). A recombinant vector having a gene construction substance for expression including this DNA and various regulator elements (including promoter, ribosome binding site, terminator, enhancer, various cis-elements for controlling the expression level) is constructed in accordance with the host cell.

This recombinant vector is transduced into a predetermined host cell (e.g., yeast, insect cell, plant cell, mammalian cell) by a regular technique, and tissues or organisms including the host cell or the cell are cultured under predetermined conditions. Thus, a desired polypeptide can be expressed and produced in the cell. Then, a polypeptide is isolated from the host cell (from a medium when secreted) and purified, so that a desired antimicrobial polypeptide can be obtained. For example, a fusion protein expression system can be utilized for efficient mass production in a host cell. In other words, a gene (DNA) encoding an amino acid sequence of a desired polypeptide is chemically synthesized, and the synthesized gene is introduced into a preferable site of a suitable vector for expression of a fusion protein (e.g., a vector for expression of GST (Glutathione S-transferase) fusion protein such as pET series provided by Novagen and pGEX series provided by Amersham Bioscience). Then, the host cell (typically *E. coli*) is transformed by the vector. The obtained transformant is cultured so that a desired fusion protein is prepared. Then, the protein is extracted and purified. Then, the obtained purified fusion protein is cleaved by a predetermined enzyme (protease) and the separated desired peptide fragment (designed antimicrobial polypeptide) is collected by an affinity chromatography or the like. The antimicrobial polypeptide of the present invention can be produced by using such a conventionally known system for expression of a fusion protein (e.g., GST/His system provided by Amersham Bioscience can be utilized).

Alternatively, a template DNA for a cell-free protein synthesis system (i.e., synthesized gene fragment including a nucleotide sequence encoding an amino acid sequence of an antimicrobial polypeptide, see the examples described later) is constructed, and various compounds (ATP, RNA polymerase, amino acids and the like) are used, so that a targeted polypeptide can be synthesized in vitro by using a so-called cell-free protein synthesis system. Regarding the cell-free protein synthesis system, for example, an article by Shimizu et al. (Shimizu et al., Nature Biotechnology, 19, 751-755 (2001)), an article of Madin et al. (Madin et al., Proc. Natl. Acad. Sci. USA, 97(2), 559-564 (2000)) can be referred to. At the time of filing the present application, a large number of enterprises already have been entrusted with production of protein (polypeptide) based on the technologies described in these articles, and kits for cell-free protein synthesis (e.g., PROTEIOS (trademark) Wheat germ cell-free protein synthesis kit available from TOYOBO Co., Ltd. in Japan) are commercially available.

Therefore, once an amino acid sequence of an antimicrobial polypeptide is determined and designed as described above, then a desired polypeptide can be easily produced by a cell-free protein synthesis system according to the amino acid sequence. For example, the polypeptide of the present invention can be easily produced based on PURESYSTEM (registered trademark) of POST GENOME INSTITUTE CO. LTD. in Japan.

A polynucleotide of a single strand or a double strand constituted substantially of a nucleotide sequence encoding the antimicrobial polypeptide of the present invention and/or a nucleotide sequence complementary to this sequence can be produced (synthesized) by a conventionally known method. In other words, a nucleotide sequence corresponding to the amino acid sequence of the antimicrobial polypeptide can be easily determined and provided by selecting a codon corresponding to each amino acid residues constituting the designed amino acid sequence. Then, once the nucleotide sequence is determined, then a polynucleotide (single strand) corresponding to the desired nucleotide sequence can be easily obtained by utilizing a DNA synthesis machine or the like. Furthermore, a targeted double strand DNA can be obtained by using various enzymatic synthesis means (typically PCR), using the obtained single strand as a template.

The polynucleotide provided by the present invention may be in the form of DNA or RNA (mRNA or the like). The DNA can be provided in the form of a double strand or a single strand. When it is provided in the form of a single strand, it may be in the form of a code chain (sense chain) or may be non-code chain (anti-sense chain) that is complementary thereto.

The polynucleotide provided by the present invention can be used as a material for constructing a recombinant gene (expression cassette) for expressing a polypeptide in various host cells or cell-free protein synthesis systems.

For example, a recombinant vector having a gene construction substance for foreign peptide expression can be constructed, using a polynucleotide having a nucleotide sequence encoding the antimicrobial polypeptide of the present invention and various regulator elements (including promoter, ribosome-binding site, terminator, enhancer, various cis-elements for controlling the expression level, etc.) for expressing the amino acid sequence in a host cell. The kinds of the regulatory elements used for constituting or constructing a vector can differ with the type of the targeted host cell. To construct a recombinant vector, polynucleotide restriction by various restriction enzymes or polynucleotide ligation that is known in the genetic engineering can be used. These techniques can be performed easily by utilizing various commercially available apparatuses.

As a method for constructing a recombinant vector and a method for introducing the constructed recombinant vector into a host cell, methods conventionally performed in the art can be used as they are, and such methods do not characterize the present invention, and therefore the detailed description thereof will be omitted.

Some of the polynucleotides provided by the present invention encode an antimicrobial polypeptide of a novel amino acid sequence.

For example, an artificially synthesized polynucleotide that does not naturally occur is provided that contains a nucleotide sequence and/or a nucleotide sequence complementary to this sequence (or substantially consists of these sequences), the nucleotide sequence encoding the antimicrobial polypeptide provided with the following requirements (a) and (b):

(a) The total number of the amino acid residues constituting a peptide chain is 5 or more and 100 or less; and
(b) Containing at least one kind of amino acid sequence shown by either one selected from the group consisting of Sequence Nos. 83, 84, 85, 86, 87, 88, 89, 90, 91, 92, 93, 94, 95, 96, 97, 98, 99, 100, 101, 102, 103, 104, 105, 106, 107, 108, 109, 110, 112, 114 and 116, or a modified sequence formed by substituting, deleting and/or adding one to several amino acid residues in this sequence.

Furthermore, an artificially synthesized polynucleotide that does not naturally occur is provided that contains a nucleotide sequence and/or a nucleotide sequence complementary to this sequence (or substantially consists of these sequences), the nucleotide sequence encoding the antimicrobial polypeptide substantially consisting of at least one kind of amino acid sequence shown by either one selected from the group consisting of Sequence Nos. 83, 84, 85, 86, 87, 88, 89, 90, 91, 92, 93, 94, 95, 96, 97, 98, 99, 100, 101, 102, 103, 104, 105, 106, 107, 108, 109, 110, 112, 114 and 116 or a modified sequence formed by substituting, deleting and/or adding one to several amino acid residues of this sequence.

The antimicrobial polypeptide of the present invention has a relatively broad antimicrobial spectrum, and can be used preferably as the main component of an antimicrobial agent (pharmaceutical composition). For example, it can be used for the purpose of treating bacterial infection, sanitizing an injured surface, preventing eye diseases, cleaning an oral cavity (gargling), preventing decay of foods, retaining freshness, removing odor, bacteriocide or bacteriostat for the surface of furniture or sanitary equipment and the like.

As a carrier contained in an antimicrobial agent, in addition to the antimicrobial polypeptide, that is, a secondary component (typically pharmaceutically acceptable), various filling agents, fillers, binders, moisturizers, surfactants, excipients, pigments, fragrances or the like can be used, depending on the use or the form of the antimicrobial agent.

There is no particular limitation regarding the form of the antimicrobial agent. For example, examples of a typical form of medicines for internal or external use include ointment, liquid medicine, suspension, emulsion, aerosol, foam, granule, powder, tablet, and capsule. Furthermore, in order to use it for injection, it can be produced in the form of a freeze dried substance or a granulated substance that is to be dissolved in a physiological saline immediately before use so as to prepare a medical fluid.

The process itself in which various forms of pharmaceuticals are prepared using materials including the antimicrobial polypeptide (main component) and various carriers (secondary component) can be performed according to a conventionally known method, and this does not characterize the present invention so that the detailed description thereof will be omitted.

As a detailed information source for prescription, for example, "Comprehensive Medicinal Chemistry" edited by Corwin Hansch and published by Pergamon Press (1990) can be referred to.

The antimicrobial agent provided by the present invention can be used by a method or a dose in accordance with the form and the purpose thereof. For example, a liquid agent can be administered intravenously, intramuscularly, subcutaneous, intracutaneous or intraperitoneal injection, or by enema to a patient. Alternatively, the agent can be administered orally when it is in a solid form such as a tablet. When it is used for the purpose of sanitizing (sterilizing) the surface of sanitary ceramic ware or preventing decay of foods, a liquid agent containing a relatively large amount (e.g., 1 to 100 mg/mL) of peptide can be sprayed directly onto the surface of a targeted object, or the surface of a targeted object can be wiped with fabric or paper impregnated with the liquid agent. These are only examples, and the same form and usage as those of conventional peptide based antibodies, agricultural chemicals, quasi-drugs or the like having a peptide as a component can be applied.

For example, for cancer patients that are subjected to radiotherapy or aids patients, prevention and treatment of bacterial infection are important concerns. The antimicrobial polypeptide provided by the present invention can exhibit the antimicrobial effect selectively with respect to the bacterium. Therefore, the antimicrobial polypeptide of the present invention is useful as a main component of an antimicrobial agent.

The polynucleotide encoding the antimicrobial polypeptide of the present invention can be used as a material used for so-called gene therapy. For example, a gene (typically DNA segment, or RNA segment) encoding the antimicrobial polypeptide is incorporated into a suitable vector, and transduced into a targeted site, so that the antimicrobial polypeptide of the present invention can be expressed constantly in an organism (cell). Therefore, the polynucleotide (DNA segment, RNA segment or the like) encoding the antimicrobial polypeptide of the present invention provided by the present invention is useful as a pharmaceutical for preventing or treating bacterial infection to the above-described patients or the like.

It is important to prevent bacterial infection during culture of skin, bone or various organs in the field of regenerative medicine. The antimicrobial polypeptide provided by the present invention has a very low toxicity (see the examples described later) with respect to the mammal cells or tissues and exhibits an antimicrobial effect selectively with respect to the bacterium. Therefore, this is very useful as a pharmaceutical for preventing bacterial infection of a cultured organ or the like. For example, as shown in the examples later, bacterial infection of an organ during culture can be prevented by adding the antimicrobial polypeptide of the present invention by itself or an antimicrobial agent having the polypeptide as one of the main components in an appropriate concentration in a culture solution.

Furthermore, with respect to cultured cells or cultured tissues, the polynucleotide encoding the antimicrobial polypeptide of the present invention can be used as a material used for gene therapy. For example, a gene (typically DNA segment, or RNA segment) encoding the antimicrobial polypeptide of the present invention is incorporated into a suitable vector, and transduced into a targeted cultured tissue, so that the antimicrobial polypeptide of the present invention can be expressed constantly or in a desired period in a cultured tissue (or cell). Therefore, the polynucleotide (DNA segment, RNA segment or the like) encoding the antimicrobial polypeptide of the present invention provided by the present invention is useful as a pharmaceutical for preventing or treating bacterial infection of cultured tissues.

Hereinafter, several examples of the present invention will be described, but they are not intended to limit the present invention.

EXAMPLE 1

Chemical Synthesis of Antimicrobial Polypeptide

Thirty-six types of polypeptide (samples 1 to 33, comparative samples 1 to 3) were produced with a peptide synthesis machine that will be described later. Table 1 shows the amino acid sequences of these polypeptides.

TABLE 1

| sample No. | amino acid sequence | total number of amino acid residues |
|---|---|---|
| sample 1 | PKKKRKV (sequence No. 4) | 7 |
| sample 2 | RQARRNRRRWR (sequence No. 21) | 12 |
| sample 3 | RIRKKLR (sequence No. 43) | 7 |
| sample 4 | PPRKKRTVV (sequence No. 28) | 9 |
| sample 5 | RKKRRQRRR (sequence No. 20) | 9 |
| sample 6 | PRRRK (sequence No. 26) | 5 |
| sample 7 | RKKKRKV (sequence No. 83) | 7 |
| sample 8 | PKKKRKVLPPLERLTL (sequence No. 84) | 16 |
| sample 9 | LPPLERLTLPKKKRKV (sequence No. 85) | 16 |
| sample 10 | RQARRNRRRWRLPPLERLTLD (sequence No. 86) | 22 |
| sample 11 | PKKKRKVLPPLERLTLPKKKRKV (sequence No. 87) | 23 |
| sample 12 | RKKKRKVLPPLERLTL (sequence No. 88) | 16 |
| sample 13 | LPPLERLTLRKKKRKV (sequence No. 89) | 16 |
| sample 14 | RKKKRKVLALKLAGLDI (sequence No. 90) | 17 |
| sample 15 | LALKLAGLDIRKKKRKV (sequence No. 91) | 17 |
| sample 16 | PKKKRKVPKKKRKV (sequence No. 92) | 14 |
| sample 17 | RIRKKLRRIRKKLR (sequence No. 93) | 14 |
| sample 18 | PRRRKPRRRK (sequence No. 95) | 10 |
| sample 19 | PKKKRKVPPRKKRTVV (sequence No. 97) | 16 |
| sample 20 | RKKKRKVRKKKRKV (sequence No. 98) | 14 |
| sample 21 | RKKKRKVRKKKRKVRKKKRKV (sequence No. 99) | 21 |
| sample 22 | RKKKRKVRKKKRKVRKKKRKVRKKKRKV (sequence No. 100) | 28 |
| sample 23 | PRRRK (sequence No. 101) | 5 |
| sample 24 | RKKKRKV (sequence No. 102) | 7 |
| sample 25 | RKKKRKVRKKKRKV (sequence No. 103) | 14 |
| sample 26 | PKKKRRV (sequence No. 104) | 7 |
| sample 27 | LKRKLQR (sequence No. 50) | 7 |

TABLE 1-continued

| sample No. | amino acid sequence | total number of amino acid residues |
|---|---|---|
| sample 28 | RKKKRKVVKRKKKR (sequence No. 105) | 14 |
| sample 29 | RKKKRKVKRKKKR (sequence No. 106) | 13 |
| sample 30 | LKRKLQRLKRKLQR (sequence No. 107) | 14 |
| sample 31 | PKKKRKVALGKLALGKL (sequence No. 108) | 17 |
| sample 32 | RQARRNRRRRWRIAGKI (sequence No. 109) | 17 |
| sample 33 | MRKKKRKVRKKKRKV (sequence No. 110) | 15 |
| comparative sample 1 | RKRR (sequence No. 27) | 4 |
| comparative sample 2 | LPPLERLTL (sequence No. 81) | 9 |
| comparative sample 3 | LALKLAGLDI (sequence No. 82) | 10 |

Sample 1 and 6 and 27 shown in Table 1 are polypeptides consisting of only one unit of a native type NLS that is different from each other.

Sample 7 is a polypeptide consisting of a modified sequence (RKKKRKV: Sequence No. 83) in which proline, which is the N-terminal amino acid in the amino acid sequence (PKKKRKV: Sequence No. 4) of the sample 1, is substituted with arginine.

Samples 8 to 11 are polypeptides consisting of a sequence in which NLS and a general NES are linked in tandem. More specifically, in sample 8, NES (LPPLERLTL: Sequence No. 81) is adjacent to the C-terminal side of the NLS (PKKKRKV: Sequence No. 4). On the other hand, in sample 9, the NLS (PKKKRKV: Sequence No. 4) is adjacent to the C-terminal side of NES (LPPLERLTL: Sequence No. 81). In sample 10, NES (LPPLERLTL: Sequence No. 81) is adjacent to the C-terminal side of the NLS (RQARRNRRRRWR: Sequence No. 21), and to the C-terminal thereof, one aspartic acid is further added. In sample 11, NES (LPPLERLTL: Sequence No. 81) is adjacent to the C-terminal side of the NLS (PKKKRKV: Sequence No. 4), and to the C-terminal side thereof, NLS (PKKKRKV: Sequence No. 4) is further added.

Samples 12 to 15 are polypeptides consisting of a sequence in which modified NLS (RKKKRKV: Sequence No. 83) of sample 7 and a general NES are linked. More specifically, in sample 12, NES (LPPLERLTL: Sequence No. 81) is adjacent to the C-terminal side of the modified NLS (RKKKRKV: Sequence No. 83). On the other hand, in sample 13, the modified NLS (RKKKRKV: Sequence No. 83) is adjacent to the C-terminal side of the NES (LPPLERLTL: Sequence No. 81). In sample 14, another NES (LALKLAGLDI: Sequence No. 82) is adjacent to the C-terminal side of the modified NLS (RKKKRKV: Sequence No. 83). On the other hand, in sample 15, the modified NLS (RKKKRKV: Sequence No. 83) is adjacent to the C-terminal side of the NES (LALKLAGLDI: Sequence No. 82).

Samples 16 to 22 and 30 are polypeptides consisting of a sequence in which two or more units of NLS or modified NLS are linked. More specifically, in sample 16, two units of NLS (PKKKRKV: Sequence No. 4) are linked. In sample 17, two units of NLS (RIRKKLR: Sequence No. 43) are linked. In sample 18, two units of NLS (PRRRK: Sequence No. 26) consisting of five amino acid residues are linked. In sample 30, two units of NLS (LKRKLQR: Sequence No. 50) are linked. In sample 19, one unit each of two different NLS (PKKKRKV: Sequence No. 4 and PPRKKRTVV: Sequence No. 28) are linked in tandem.

In samples 20, 21 and 22, two, three and four units of the modified NLS (RKKKRKV: Sequence No. 83) are linked, respectively.

In sample 23, the carboxyl group of the C-terminal amino acid of NLS (PRRRK: Sequence No. 26) is amidated.

In sample 24, the carboxyl group of the C-terminal amino acid of the modified NLS (RKKKRKV: Sequence No. 83) is amidated.

In sample 25, the carboxyl group of the C-terminal amino acid of a sequence (RKKKRKVRKKKRKV: Sequence No. 98) in which two units of the modified NLS (RKKKRKV: Sequence No. 83) are linked is amidated.

Sample 26 is a polypeptide consisting of a sequence (PKKKRRV: Sequence No. 104) in which "lysine" that is the sixth amino acid residue from the N-terminal side of the amino acid sequence (PKKKRKV: Sequence No. 4) of sample 1 is conservatively substituted with "arginine".

Sample 28 is a polypeptide in which seven amino acid residues that are rich with basic amino acid are added to the C-terminal side of the modified NLS (RKKKRKV: Sequence No. 83) of sample 7. More specifically, a sequence (VKRKKKR) in which the modified NLS (RKKKRKV: Sequence No. 83) is inversed is added.

Sample 29 is a polypeptide in which six amino acid residues (KRKKKR) that are all basic amino acids are added to the C-terminal side of the modified NLS (RKKKRKV: Sequence No. 83) of sample 7.

Sample 31 is a polypeptide in which ten amino acid residues (ALGKLALGKL) are added to the C-terminal side of the NLS (PKKKRKV: Sequence No. 4) of sample 1.

Sample 32 is a polypeptide in which five amino acid residues (IAGKI) are added to the C-terminal side of the NLS (RQARRNRRRRWR: Sequence No. 21) of sample 2.

Sample 33 is a polypeptide in which two units of the modified NLS (RKKKRKV: Sequence No. 83) of sample 7 are linked and further a methionine group is added to the N-terminal side thereof.

In this example, in order to compare the polypeptides of the above-described samples regarding the antimicrobial activities described later, three types of polypeptide that do not belong to the range of the present invention were synthesized.

Specifically, comparative sample I is a polypeptide consisting only of one unit of a short NLS (RKRR: Sequence No. 27) consisting of four amino acid residues.

Comparative samples 2 and 3 are polypeptides consisting only of one unit of different NESs (LPPLERLTL: Sequence No. 81, LALKLAGLDI: Sequence No. 82), respectively, and do not contain NLS.

The above-described polypeptides (see Table 1 and the sequence listing with respect to each amino acid sequence) were synthesized by a solid synthesis method (Fmoc method) using a commercially available peptide synthesis machine (PEPTIDE SYNTHESIZER 9050 manufactured by PerSeptive Biosystems). As a condensing agent, HATU (Applied Biosystems product) was used, and the resin and the amino acids used in the solid synthesis method were purchased from NOVA biochem. To amidate the C-terminal of the amino acid sequence, "Rink Amide resin (100 to 200 mesh)" was used as the solid carrier.

Thus, a peptide chain is elongated from Fmoc-amino acid that is bonded to a resin by repeating deprotection reaction and condensation reaction according to the synthesis program of the peptide synthesizing machine, so that a synthesized peptide of a targeted length was obtained. More specifically, Fmoc, which is an amino protecting group of an amino acid, is cleaved and removed with 20% piperidine/dimethylformamide (DMF) (peptide synthesis grade manufactured by KANTO KAGAKU), cleaned with DMF, reacted with 4eq of Fmoc-amino acid (—OH) each, and cleaned with DMF. This operation was repeated. Then, after all the elongation reaction of the peptide chain was completed, the Fmoc group was cleaved with 20% piperidine/DMF, and the above-described reaction product was cleaned with DMF and methanol in this order.

After solid synthesis, the synthesized peptide chain and the resin were both transferred to a centrifuge tube, and 1.8 mL of ethanediol, 0.6 mL of m-cresol, 3.6 mL of thioanisole, and 24 mL of trifluoroacetic acid were added thereto, and then the mixture was stirred at room temperature for two hours. Thereafter, resin bonded to the peptide chain was filtrated and removed.

Then, cooled ethanol was added to the filtrate, and a peptide precipitate was obtained by cooling with iced water. Thereafter, the supernatant was discarded by centrifugation (for five minutes at 2500 rpm). Cool diethyl ether was freshly added to the precipitate and stirred sufficiently, and then centrifugation was performed in the same conditions as above. This process of stirring and centrifugation was repeated in total of three.

The obtained peptide precipitate was vacuum-dried and purified with a high speed liquid chromatography (Waters 600 manufactured by Waters Corp.).

More specifically, pre-column (Guard-Pak Deltapak C18A300 manufactured by Nippon Waters) and C18 reverse phase column (Wakopak WS-DHA 4.6×150 mm ODS-C18 manufactured by Wako Pure Chemical Industries Ltd.) were used, and a mixed solution of 0.1% trifluoroacetic acid (TFA) aqueous solution and 0.1% trifluoroacetic acid acetonitrile solution was used as an eluent. In other words, separation and purification were performed for 30 to 40 minutes using the above-described columns at a flow rate of 1.5 mL/min while increasing over time the amount of the trifluoroacetic acid acetonitrile solution contained in the eluent (providing the concentration gradient from 10% to 80% in volume ratio). The peptide eluted from the reverse phase column was detected at a wavelength of 220 nm using an ultraviolet ray detector (490E Detector manufactured by Waters) and shown on a recording chart as the peaks.

The molecular weight of each eluted polypeptide was determined, using Voyager DE RP (trademark) manufactured by PerSeptive Biosystems, based on MALDI-TOF MS (Matrix-Assisted Laser Desorption Time of Flight Mass Spectrometry). As a result, it was confirmed that the targeted polypeptide was synthesized and purified.

EXAMPLE 2

Antimicrobial Activity of Synthesized Polypeptide

Regarding the antimicrobial polypeptide of the present invention (samples 1 to 33) and the polypeptides of comparative samples 1 to 3, the antimicrobial activities (minimum inhibitory concentration: MIC) with respect to gram-negative bacteria (*E. coli*) and gram-positive bacteria (*S. aureus*) were determined by a liquid medium dilution technique using a 96-well microplate.

More specifically, liquid bouillon media ("NUTRIENT BROTH Dehydraged" manufactured by DIFCO) in a polypeptide concentration of 500, 250, 125, 62.5, 31.3, 15.6, 7.8, 3.9, 1.9, 1.0 and 0.5 μM were prepared, and filled in a 96-well microplate. On the other hand, bacteria suspension (about 2×10⁶ cells/mL) that had been stationary cultured at 37° C. for 18 hours with LB Broth, Lennox (manufactured by DIFCO) were inoculated to each well of the 96-well microplate in an equal amount to that of the pharmaceutical solution (the above-described polypeptide-containing bouillon medium). After inoculation, culture was started in an incubator at 37° C., and it was examined based on the turbidity after 24 hours and 48 hours whether or not bacteria are present. The minimum of the polypeptide concentrations in which no increase in the turbidity caused by bacteria at the time of measurement was observed was defined as MIC in this example.

Table 2 shows the antimicrobial activities (MIC) of each sample and comparative sample based on such an antimicrobial test. The unit of MIC in Table 2 is μM.

TABLE 2

| | antimicrobial activity (μM) | | | |
|---|---|---|---|---|
| | *E. coli* | | *S. aureus* | |
| sample No. | after 24h | after 48h | after 24h | after 48h |
| sample 1 | 62.5 | >500 | 62.5 | 125.0 |
| sample 2 | 3.9 | 3.9 | 3.9 | 3.9 |
| sample 3 | 62.5 | 62.5 | 62.5 | 62.5 |
| sample 4 | 250.0 | >500 | 125.0 | 125.0 |
| sample 5 | 1.9 | 3.9 | 15.6 | 15.6 |
| sample 6 | >500 | >500 | 250.0 | 500.0 |
| sample 7 | 62.5 | 500.0 | 15.6 | 31.3 |
| sample 8 | 31.3 | 31.3 | 3.9 | 3.9 |
| sample 9 | 31.3 | 31.3 | 3.9 | 3.9 |
| sample 10 | 3.9 | 3.9 | 1.9 | 3.9 |
| sample 11 | 3.9 | 3.9 | 1.9 | 1.9 |
| sample 12 | 15.6 | 15.6 | 3.9 | 3.9 |
| sample 13 | 15.6 | 15.6 | 3.9 | 3.9 |
| sample 14 | 3.9 | 3.9 | 1.0 | 1.9 |
| sample 15 | 3.9 | 3.9 | 1.9 | 3.9 |

TABLE 2-continued

| | antimicrobial activity (μM) | | | |
|---|---|---|---|---|
| | E. coli | | S. aureus | |
| sample No. | after 24h | after 48h | after 24h | after 48h |
| sample 16 | 1.9 | 1.9 | 7.8 | 15.6 |
| sample 17 | 1.9 | 3.9 | 3.9 | 3.9 |
| sample 18 | 3.9 | 3.9 | 7.8 | 7.8 |
| sample 19 | 3.9 | 3.9 | 7.8 | 7.8 |
| sample 20 | 1.9 | 1.9 | 1.9 | 1.9 |
| sample 21 | 1.9 | 1.9 | 0.5 | 0.5 |
| sample 22 | 1.9 | 1.9 | 1.0 | 1.0 |
| sample 23 | 31.3 | 31.3 | 7.8 | 15.6 |
| sample 24 | 3.9 | 15.6 | 1.0 | 1.0 |
| sample 25 | 3.9 | 3.9 | 1.9 | 1.9 |
| sample 26 | 62.5 | 500.0 | 125.0 | 125.0 |
| sample 27 | 500.0 | >500 | 125.0 | 125.0 |
| sample 28 | 1.0 | 1.0 | 3.9 | 7.8 |
| sample 29 | 1.0 | 1.0 | 3.9 | 7.8 |
| sample 30 | 3.9 | 3.9 | 3.9 | 3.9 |
| sample 31 | 7.8 | 7.8 | 3.9 | 7.8 |
| sample 32 | 3.9 | 3.9 | 1.9 | 1.9 |
| sample 33 | 3.9 | 3.9 | 1.9 | 1.9 |
| comparative sample 1 | >500 | >500 | >500 | >500 |
| comparative sample 2 | >500 | >500 | >500 | >500 |
| comparative sample 3 | >500 | >500 | >500 | >500 |

As seen from the results shown in Table 2, all of the polypeptides of the present invention (samples 1 to 33) exhibited higher antimicrobial activities, compared with the control polypeptides (comparative samples 1 to 3).

In the polypeptide (samples 10, 14, 15, etc.) in which NLS and NES are arranged in proximity, high antimicrobial activities were exhibited with respect to both gram-positive bacteria and gram-negative bacteria. The polypeptide (e.g., samples 16 to 22) in which two or more units of NLSs are arranged in tandem exhibited particularly high antimicrobial activities.

The polypeptides (e.g., samples 2, 5, 16 to 22, 28, and 29) that contained at least one unit of NLS or modified NLS and were rich with basic amino acid residues (having preferably 8 or more basic amino acid residues) exhibited particularly high antimicrobial activities. Furthermore, it was confirmed that the polypeptide (sample 24) in which the C-terminal was amidated had higher antimicrobial activities than those of the polypeptide (sample 7) of the same sequence in which the C-terminal was not amidated.

The results of Table 2 confirmed that the antimicrobial polypeptide of the present invention had excellent antimicrobial activities and broad antimicrobial spectrum.

EXAMPLE 3

Antimicrobial Spectrum

Next, regarding the polypeptides of the samples 16, 17, 10, 14, and 20, the same antimicrobial test (MIC measurement test) as in Example 2 was performed with respect to various bacteria (see Table 3), and the antimicrobial spectra of these polypeptides were evaluated. As a result, as shown in Table 3, it was confirmed that the antimicrobial polypeptide of the present invention had antimicrobial activities with respect to a wide range of gram-positive bacteria and gram-negative bacteria.

TABLE 3

| | antimicrobial activity after 24 hours: MIC (μM) | | | | |
|---|---|---|---|---|---|
| bacteria tested | sample 16 | sample 17 | sample 10 | sample 14 | sample 20 |
| Bacillus cereus IFO3001 | >286.0 | >260.3 | 21.4 | 32.0 | >267.9 |
| Bacillus cereus IFO15305 | >286.0 | >260.3 | 42.9 | 64.1 | 133.9 |
| Bacillus pumilus IFO3813 | 143.0 | 16.3 | 5.4 | 4.0 | 16.7 |
| Bacillus brevis IFO15304 | >286.0 | >260.3 | 21.4 | 128.2 | 133.9 |
| Bacillus subtilis ATCC6633 | 2.2 | 1.0 | 0.7 | 1.0 | 2.1 |
| Bacillus subtilis IFO3134 | 8.9 | 0.5 | 0.7 | 1.0 | 4.2 |
| Micrococcus luteus IFO12708 | 8.9 | 4.1 | 5.4 | 4.0 | 8.4 |
| Staphylococcus aureus COL (MRSA) | >286.0 | 16.3 | 10.7 | 16.0 | 33.5 |
| Staphylococcus aureus RN450 (*MSSA) | 71.5 | 32.5 | 10.7 | 16.0 | 33.5 |
| Staphylococcus aureus IFO12732 | 71.5 | 2.0 | 1.3 | **/ | 4.2 |
| Staphylococcus aureus IID1677 (MRSA) | 35.7 | 8.1 | 10.7 | **/ | 8.4 |
| Escherichia coli IFO12713 | 8.9 | 8.1 | 10.7 | 8.0 | 8.4 |
| Escherichia coli O157:H7 sakai | 17.9 | 8.1 | 10.7 | 8.0 | 8.4 |
| Escherichia coli O26:H11 | 17.9 | 8.1 | 10.7 | 16.0 | 8.4 |
| Klebsiella pneumoniae ATCC4352 | 8.9 | 8.1 | 10.7 | 32.0 | 4.2 |
| Proteus vulgaris ATCC13315 | 8.9 | 8.1 | 10.7 | 64.1 | 8.4 |
| Pseudomonas aeruginosa ATCC10145 | 4.5 | 8.1 | 10.7 | 32.0 | 4.2 |
| Pseudomonas aeruginosa IFO3080 | 8.9 | 8.1 | 10.7 | 16.0 | 4.2 |
| Salmonella enteritidis IFO3313 | 2.2 | 4.1 | 10.7 | 32.0 | 4.2 |
| Salmonella typhimurium IFO1324 | 35.7 | 4.1 | 10.7 | >256.3 | 8.4 |

EXAMPLE 4

Safety Test with Respect to Mammal

The toxicity test with respect to mammalian cells was performed as follows.

A172 (human neuroglioma) cells were planted in 8×10³ per one well of the 96-well plate on the previous day and ware statically cultured at 37° C. at 5% $CO_2$. Next day, the medium was removed and the cells were cleaned once with PBS, and then serum-free medium (a medium "RPMI1640" manufactured by GIBCO BRL, to which serum was not added) containing polypeptide (either one of the samples 1 to 26) in a concentration of 0, 0.5, 5, 25, 50, 100, 200, and 400 μg/mL was added in an amount of 100 μl per well (the number of wells per sample (n)=1 or 2). Thereafter, it was statically cultured for 24 hours in the same conditions as above.

After the end of culture, the medium was removed, and the cells were cleaned once with PBS. Then, a DMEM medium (containing 10% FBS) manufactured by GIBCO BRL containing 5% WST-8 (reagent for cell growth measurement manufactured by Kishida Chemical Co. Ltd.) was added in an amount of 100 μl per well, and statically cultured for one hour under the same conditions above. Thereafter, the absorbance was measured at a measurement wavelength of 450 nm and a reference wavelength of 600 nm, using a plate reader. The relative cell viability in each polypeptide concentration was obtained, taking the absorbance of a sample of polypeptide in 0 μg/mL (i.e., no polypeptide added) as 100%. Herein, the samples having a relative cell viability of 80% or more at a polypeptide concentration of 100 μg/mL were denoted as "nontoxic", and the samples having a relative cell viability of less than 80% were denoted as "toxic". As a result, all of the polypeptides (samples 1 to 26) were nontoxic.

Furthermore, six kinds of peptide-containing injection liquid (solvent: physiological saline) containing the samples 10, 12, 13, 14, 15 and 20, respectively, were prepared. They were intraperitoneally injected to mice and $LD_{50}$ values were obtained.

As a result, all of the $LD_{50}$ of the antimicrobial polypeptides that were tested were larger than 150 mg/kg. That is to say, it was confirmed that the toxicity of the antimicrobial polypeptide of the present invention with respect to mammal was very low.

EXAMPLE 5

Preparation of Granules

After 50 mg of polypeptide of the sample 20 were mixed with 50 mg of crystallized cellulose and 400 mg of lactose, 1 mL of a mixed solution of ethanol and water was added and the mixture was kneaded. This kneaded product was granulated according to a regular method, and thus a granule having the antimicrobial polypeptide as the main component was obtained.

EXAMPLE 6

Genetic Engineering Synthesis (1) of Antimicrobial Polypeptide

Single strand DNAs consisting of the nucleotide sequence shown in Sequence Nos. 111, 113 and 115 in the sequence listing were synthesized, using a commercially available nucleic acid synthesis machine ("ABI3900" manufactured by Applied Biosystems) according to the usage manual. Furthermore, as primers for forming a double strand DNA based on these DNAs, one kind of forward primer (Sequence No. 117) and three kinds of reverse primers (Sequence Nos. 118, 119 and 120) were chemically synthesized. Each reverse primer of Sequence Nos. 118, 119 and 120 was used for synthesizing a double strand DNA of the sequences shown in Sequence Nos. 111, 113 and 115, respectively.

Double strand DNAs containing the nucleotide sequences shown in Sequence Nos. 111, 113 and 115 in the sequence listing were synthesized by a general polymerase chain reaction (e.g., the description in "PCR protocols: Current Methods and Applications", edited by White, published by Humana Press (1993) can be referred to), using these primers.

The double strand DNAs shown in Sequence Nos. 111, 113 and 115 have encoded the antimicrobial polypeptide of the amino acid sequences shown in Sequence Nos. 112, 114 and 116, respectively, and have a promoter sequence on the upstream side (5' terminal side) of the code region and have a stop codon on the downstream side (3' terminal side).

Next, a polypeptide whose amino acid sequence was MPKKKRKVLPPLERLTLPKKKRKV (Sequence No. 116) was synthesized by a cell-free protein synthesis system (cell-free expression system), using the DNA of the nucleotide sequence shown in Sequence No. 115 as the template, according to the protocol described in the article of Shimizu et al. (Shimizu et al., Nature Biotechnology, 19, 751-755 (2001)).

More specifically, 50 μl (pH 7.3) of a reaction liquid containing the following components was prepared: 9 mM magnesium acetate, 5 mM potassium phosphate, 95 mM potassium glutamate, 5 mM ammonium chloride, 0.5 mM calcium chloride, 1 mM spermidine, 8 mM putrescine, 1 mM dithiothreitol (DTT), 2 mM of ATP, 2 mM of GTP, 1 mM of CTP, 1 mM of UTP, 10 mM creatine phosphate, 2.8 units ($A_{260}$) of tRNA mixture (manufactured by Roche), 0.5 μg of 10-formyl-5,6,7,8-tetrahydrofolic acid, 0.1 mM of each amino acid, 12 picomoles of ribosome and various enzymes and factors provided with His-tag (that is, 1 μg of initiation factor 1 (IF1), 2 μg of IF2, 0.75 μg of IF3, 1 μg of elongation factor-G (EF-G), 2 μg of EF-Tu, 1 μg of EF-Ts, 0.5 μg of termination factor 1 (RF1), 0.5 μg of RF3, 0.5 μg of RRF, 30 to 300 units each of aminoacyl-tRNA synthetase (20 kinds in total) and methionyl-tRNA transformilase, 0.2 μg of creatine kinase (manufactured by Roche), 0.15 μg of myokinase (manufactured by Sigma), 0.054 μg of nucleoside diphosphatekinase, 0.1 units of pyrophosphatase (manufactured by Sigma), and 0.5 μg of T7 RNA polymerase. This reaction liquid was incubated at 37° C. for 5 minutes. Thereafter, the template DNA was added to this reaction liquid, and incubated at 37° C. for 1 hour. Thereafter, the reaction liquid was transferred to be in ice to stop the synthesis reaction of the peptide.

Then, the reaction liquid was filled in a device for ultrafiltration (Amicon (registered trademark) Centricon (registered trademark) YM-100 device, manufactured by Millipore Corporation) and subjected to centrifugation so that an eluate was collected. Then, the collected liquid was purified by affinity chromatography using Ni-NTA agalose (manufactured by Qiagen). Then, this purified liquid was subjected to SDS-PAGE, so that it was confirmed that a targeted polypeptide had been synthesized.

More specifically, a part of the collected purified liquid (containing the targeted peptide) was placed in a polyacrylamide gel having an acrylamide concentration gradient of 15 to 25% and subjected to electrophoresis at 300 V for 50 min. On this gel, in addition to the final purified liquid, a part of the reaction liquid obtained immediately after the above-described peptide synthetic reaction, that is, immediately after incubation at 37° C. for one hour and a part of the eluate after ultrafiltration were also placed at the same time. As a negative control, a reaction liquid immediately after incubation at 37° C. for one hour that was obtained by performing the same process except that the template DNA (Sequence No. 115) was not added, the eluate after ultrafiltration and the purified liquid were placed on the same gel. Furthermore, a polypeptide (MPKKKRKVLPPLERLTLPKKKRKV) of Sequence No. 116 that was synthesized separately with a peptide synthesis machine (PEPTIDE SYNTHESIZER 9050 as described above) was placed on the same gel.

After electrophoresis, the gel was immersed in a stain solution (7.5% acetic acid) containing a fluorescent stain (SYPRO (trademark) Orange manufactured by Amersham Bioscience) for 40 minutes to stain the band of the peptide contained in the gel. Thereafter, the gel was immersed in 7.5% acetic acid to remove excess stain. Then, analysis was performed with an image analyzer (product name "Typhoon") manufactured by Amersham Pharmacia (excitation wavelength: 532 nm, fluorescence filter: 580BP30). FIG. 1 shows the results (image after stain). Lane 1 shown in FIG. 1 shows a migration pattern of an LMW marker (product name: LMW Marker Kit, produce code: 17-0446-01) manufactured by Amersham Bioscience, and bands of about 14.4 kDa, 20.1 kDa, 30 kDa, 45 kDa, 66 kDa, and 97 kDa from the downstream of the lane can be seen. Lane 2 shows a migration pattern of a peptide marker kit (product name: Peptide Marker Kit, produce code: 80-1129-83) manufactured by Amersham Bioscience, and bands of about 6.2 kDa, 8.2 kDa, 10.7 kDa, 14.4 kDa, and 16.9 kDa from the downstream of the lane can be seen. Lane 3 and Lane 4 show migration patterns of the reaction liquid immediately after the peptide synthesis reaction when the template DNA is contained and not contained, respectively. Lane 5 and Lane 6 show migration patterns of the eluate after ultrafiltration when the template DNA is contained and not contained, respectively. Lane 7 shows a migration pattern of the purified liquid that flowed through Ni-NTA agarose when the template DNA is contained. Lane 8 shows a migration pattern (70 ng/3.4 µl) of a polypeptide of the targeted sequence (Sequence No. 116) synthesized with a peptide synthesis machine. Lane 9 shows a migration pattern of the purified liquid that flowed through Ni-NTA agarose when the template DNA is not contained. Lane 10 shows a migration pattern of dihydrofolate reductase (DHFR) after synthesis with the same cell-free protein synthesis system (see the article of Shimizu et al.) and purification by the same process.

As seen from FIG. 1, in Lanes 3, 5 and 7 (see the arrow), a definite band is present in the same position as in Lane 8 (see the arrow). This band is not seen in Lanes 4, 6 and 9 in which the template DNA was not added.

Figure 2:
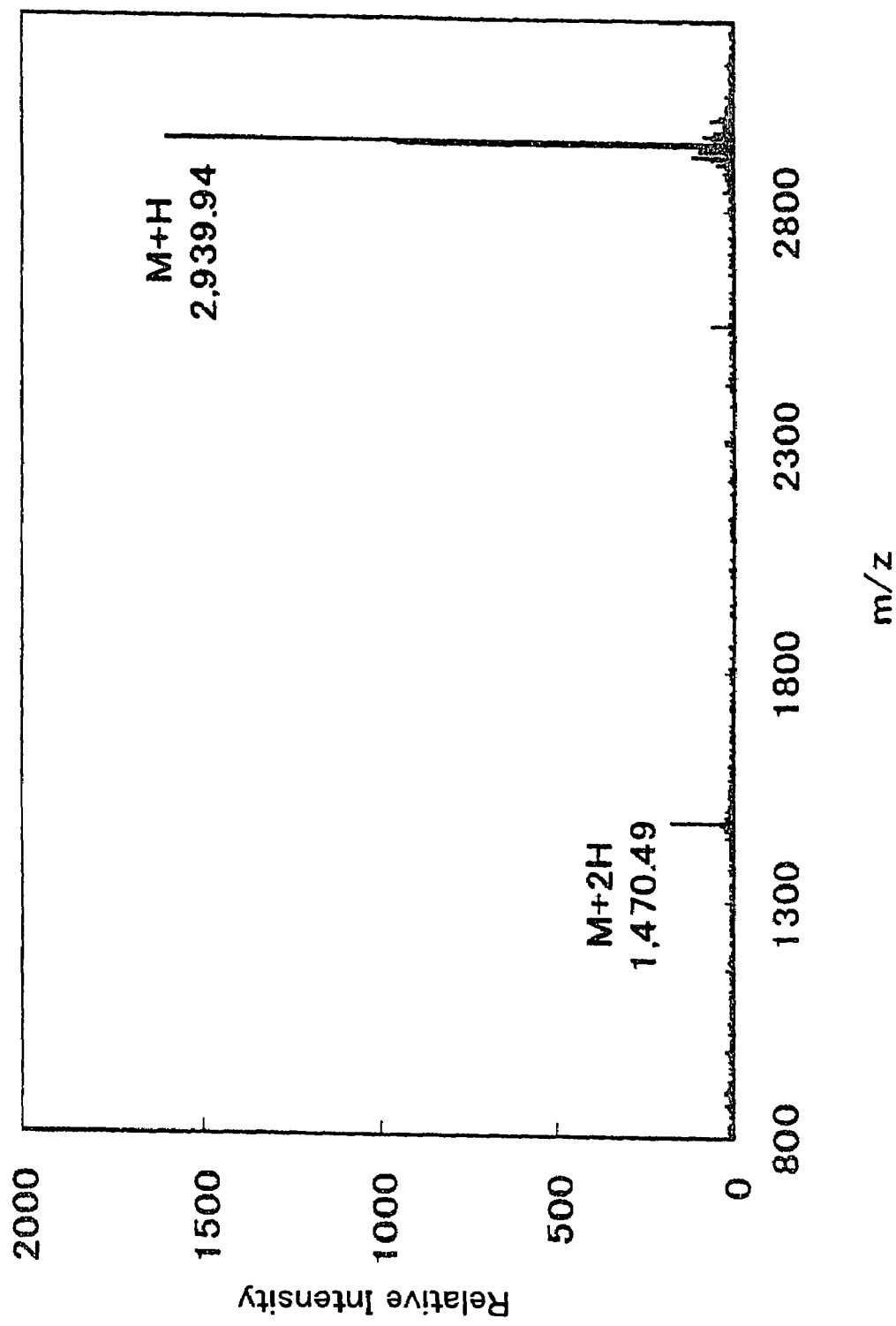
FIG. 2 is a mass spectrum showing the peaks of molecular ions obtained when a polypeptide that is synthesized by a cell-free protein synthetic system is analyzed with MALDI-TOF MS, where the horizontal axis shows the mass charge ratio (m/z), and the vertical axis shows the relative intensity.

Next, the gel was dried, and then the targeted band in Lane 7 (the band shown by the arrow in FIG. 1) was cut out, and PMF analysis (Peptide Mass Finger printing analysis) of the polypeptide was performed, using a matrix-assisted laser desorption time of flight mass spectrometry (MALDI-TOF MS: product name "Voyager RPde" manufactured by Amersham Bioscience). As a result, the peaks of molecular ions shown in FIG. 2 were seen. The observed mass number ([M+H]$^+$ =2939.94, [M+2H]$^{2+}$=1470.49) substantially matched the calculated mass number ([M+H]$^+$=2939.89, [M+2H]$^{2+}$ =1470.45). No peak indicating the presence of a peptide whose N-terminal and/or C-terminal had been degraded or a peptide having an amino acid residue that had been modified in its side chain was seen (However, the amino group of methionine in the N-terminal had been formylated normally).

Figure 3:
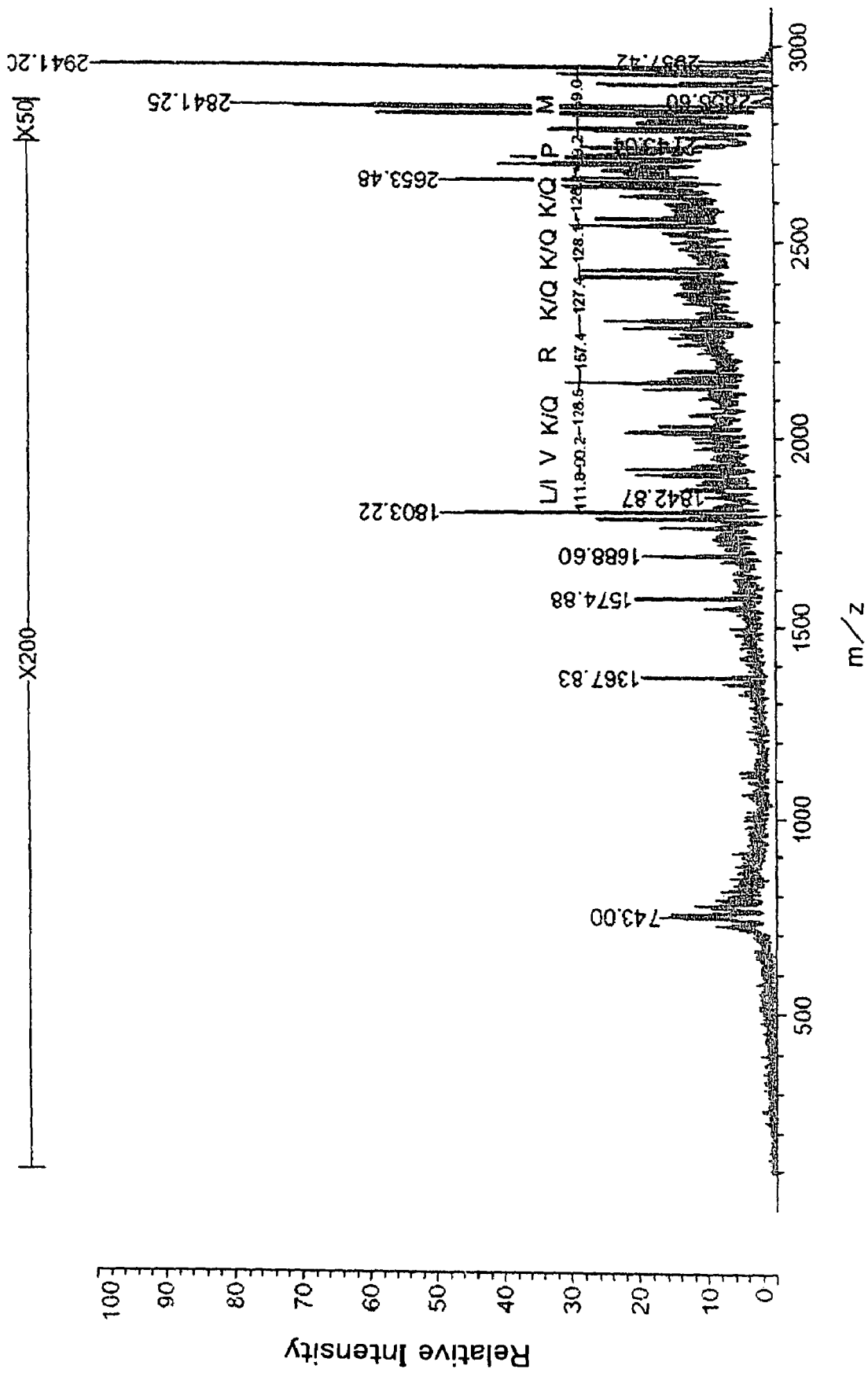
FIG. 3 is a mass spectrum showing the peaks of fragment ions obtained when a polypeptide that is synthesized by a cell-free protein synthetic system is analyzed with MALDI-TOF MS, where the horizontal axis shows the mass charge ratio (m/z), and the vertical axis shows the relative intensity.

Next, PSD (post-source decay) analysis (i.e., a method of detecting excited molecular ions that are fragmented during flight in TOF MS) was performed by driving the MALDI-TOF MS in a PSD mode. As a result, the peaks of the fragmented ions shown in FIG. 3 were obtained. By such analysis, the amino acid sequence of the targeted polypeptide in Lane 7 was identified as M-P-(K/Q)-(K/Q)-(K/Q)-R-(K/Q)-V-(L/I) sequentially from the N-terminal. This result matches the amino acid sequence of the polypeptide of Sequence No. 116.

The above results confirmed that when a template DNA is used, the antimicrobial polypeptide of the present invention can be easily synthesized and produced with a cell-free protein synthesis system as described above.

EXAMPLE 7

Genetic Engineering Synthesis (2) of Antimicrobial Polypeptide

A GST fusion protein (Glutathione S-transferase/His-Tag fusion protein) containing the sequence of the targeted polypeptide (sample 17 as above) was expressed in *E. coli*, using a recombinant DNA technique, and the collected GST fusion protein was digested with an enzyme so that the targeted polypeptide (fragment) was separated and purified.

First, single strand DNAs consisting of nucleotide sequences that are complementary each other shown in Sequence Nos. 121 and 123 were synthesized, using a commercially available nucleic acid synthesis machine ("ABI3900" manufactured by Applied Biosystems) according to the usage manual. Then, these DNAs were annealed so that a double strand DNA was obtained. Sequence No. 121 is a sequence for encoding the amino acid sequence of the polypeptide of this example, and Sequence No. 123 is its complementary sequence. The amino acid sequences of the polypeptide encoded in the synthesized polynucleotide are shown in Sequence Nos. 121 and 122. This amino acid sequence is constituted by the amino acid sequence of the sample 17 (Sequence No. 93) described above, one methionine residue positioned on the N-terminal side thereof, 6 consecutive histidine residues and one glutamic acid residue. The methionine residue is inserted so that the targeted amino acid sequence portion can be cleaved with cyanogen bromide from the fusion GST portion when the fusion protein described later is expressed in the form of being insoluble. The sequence of 6 histidine residues is a tag portion for collecting the targeted polypeptide (fragment) with affinity after the fusion GST is cleaved. Furthermore, the glutamic acid residue adjacent to the histidine is inserted in order to cleave the tag portion from the targeted polypeptide.

As seen from the sequence shown in Sequence No. 121, recognition sites of restriction enzymes EcoRI and PstI are contained in the opposite ends (i.e., upstream of the codon corresponding to methionine and downstream of the stop codon) of the synthesized polynucleotide, respectively. This double strand DNA was cleaved with the restriction enzymes EcoRI and PstI. The product digested by the restriction enzymes was subjected to agarose gel electrophoresis, and a DNA fragment having an EcoRI cleavage site and a PstI cleavage site on its opposite ends was purified.

Figure 4:
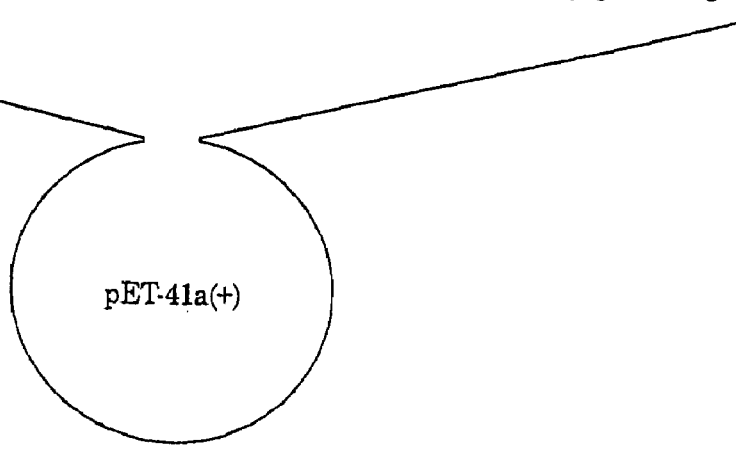
FIG. 4 is a schematic view showing the state in which the synthesized polynucleotide disclosed herein is inserted to a commercially available expression vector (pET-41a(+)).
Figure 5:
FIG. 5 is a photograph showing the results of fractionating a sample obtained by purifying a fusion protein derived from a recombinant E. coli by several processes by polyacrylamide gel electrophoresis.

Next, as shown in FIG. 4, the GST fusion protein expression vector (pET-41a(+) DNA:catalog No. 70556-3) purchased from Novagen was cleaved with restriction enzymes EcoRI and PstI, and the double strand DNA (Sequence No. 121) was ligated (inserted) in the EcoRI and PstI sites. The detailed map of the cloning/expression region of the GST fusion protein expression vector "pET-41a(+)" (entire nucleotide sequence:5933 bp) that was used is described in detail in a catalog of Novagen.

A competent cell (*E.coli* JM109) was transformed, using a plasmid that had been subjected to a ligation treatment. The obtained transformant was cultured at 37° C. in a kanamycin containing LB medium (Km$^+$), and a clone that was transformed with the plasmid in which the double strand DNA was inserted was isolated from the cultured preparation. This clone was cultured, and the plasmid in which the double strand DNA was inserted was isolated from the cultured preparation and collected. Then, the collected recombinant plasmid was used to transform *E.coli* for high expression of fusion protein (*E.coli* BL21 (DE3)). The obtained transformed product was cultured at 37° C. in a LB medium (Km$^+$), and the clone that was transformed with the plasmid in which the double strand DNA was inserted was isolated from the cultured preparation.

Next, the isolated clone was cultured at 30° C. in 3 liter of LB medium (Km$^+$). When OD$_{600}$ was 0.9, IPTG was added so that the final concentration was 0.5 mM to induce production of fusion protein. Then, after 6 hours, the cultured medium was subjected to centrifugation, and about 11.6 g of bacteria (wet state) were collected and frozen for storage.

Later, the frozen storaged bacteria were suspended in about 100 mL of PBS, and 20% TritonX-100 was added so that the final concentration was 1%. This suspension was subjected to an ultrasonic treatment to crush the bacteria. Thereafter, centrifugation was performed so that about 110 mL of the supernatant were collected. This supernatant was applied to a Glutathione Sepharose 4B column with 1 mL volume, and the column was cleaned with PBS containing 1% TritonX-100 and further was cleaned with PBS. Then, 50 mM Tris-HCl (pH8.0) containing 10 mM reduced glutathione was allowed to flow through the column so that the targeted fusion protein was eluted from the column. Thus, about 60 mg of fusion protein were obtained.

Next, the collected fusion protein solution was treated with thrombin. More specifically, thrombin having a predetermined titer (i.e., about 0.01U per 20 µg of the fusion protein) was added to a solution of the fusion protein, and left over a night at 20° C. This reaction allowed the fusion protein to be divided into a GST portion and a peptide portion containing the targeted amino acid sequence.

This protease treated solution was then applied to a Glutathione Sepharose 4B column and this passed fraction was collected. Furthermore, the column was cleaned with PBS containing 1% TritonX-100, and a part thereof (an eluted fraction in the early stage) was also collected. Then, by subjecting this collected solution to SDS-PAGE, it was confirmed that the targeted polypeptide had been collected. More specifically, a part of the collected purified liquid (containing the targeted polypeptide) was placed on a polyacrylamide gel (Multigel 15/25 manufactured by Daiich Pure Chemical Co., Ltd.) having an acrylamide concentration gradient of 15 to 25%, and subjected to electrophoresis at 30 mA for about 2 hours. Table 5 shows the results. Lane M of the gel is a migration pattern of a peptide marker (BenchMark Protein Ladder manufactured by Invitrogen), and Lane 1 is a migration pattern of a fusion protein solution before the thrombin treatment, and Lane 2 is a migration pattern of a fusion protein solution after the thrombin treatment. Lane 3 is a migration pattern of the passed fraction from the column, and Lane 4 and Lane 5 are migration patterns of a fraction of a collected cleaning liquid with which the column was cleaned. Lanes 6 to 11 are migration patterns of an eluted fraction that was portioned from the column. As shown in the figure, in Lanes 2 to 5, the band of a peptide fragment containing the targeted amino acid sequence (Sequence No. 122) that had been separated from GST was seen.

Figures 8A, 8B:
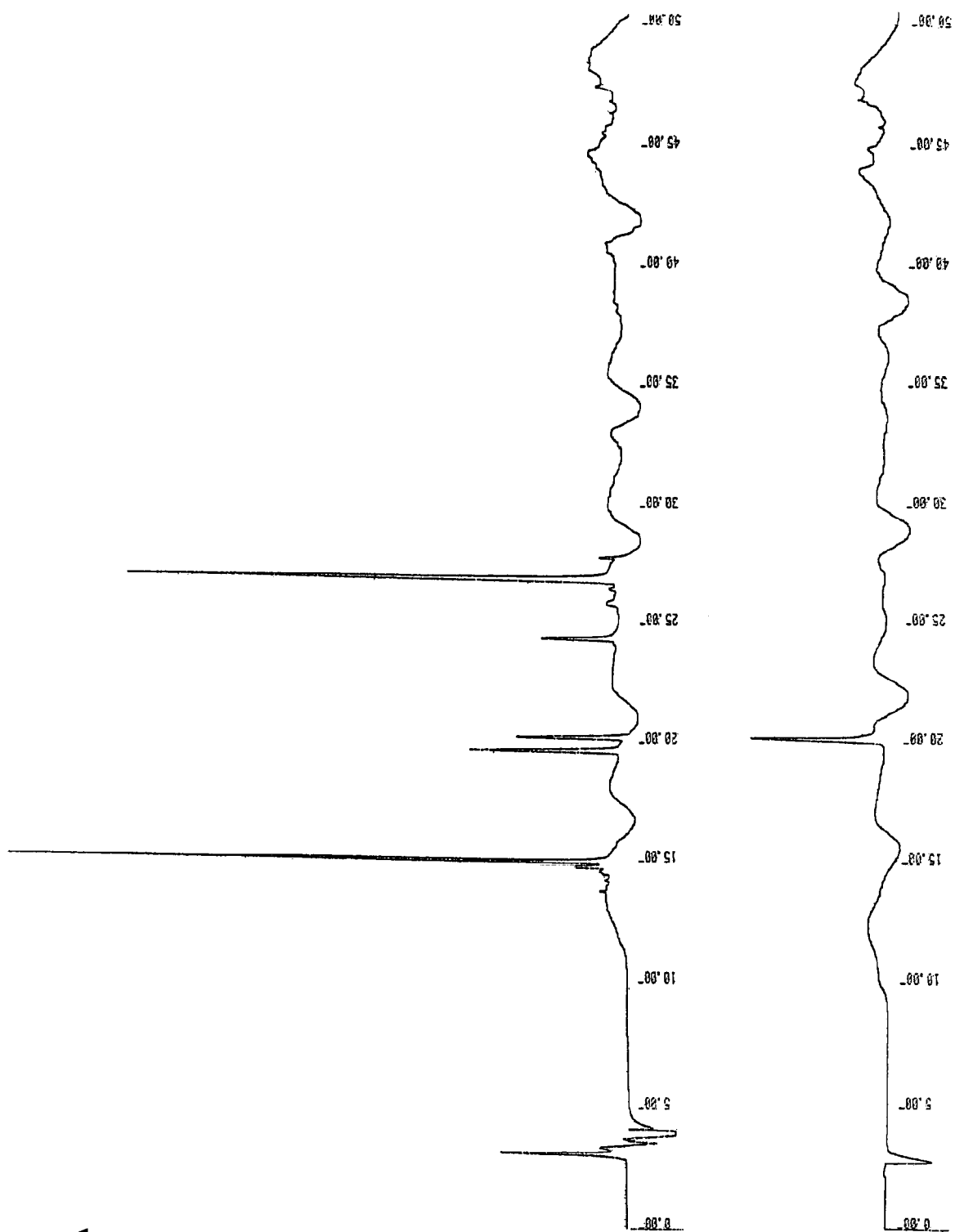
FIG. 8A is a chromatogram showing the results of analyzing a sample obtained by treating a fusion protein derived from a recombinant E. coli by several processes by reverse phase chromatograph, where the horizontal axis shows the retention time (min), and the vertical axis shows the relative intensity ($\mu$V).
FIG. 8B is a chromatogram showing the results of analyzing a chemically synthesized polypeptide sample by reverse phase chromatograph, where the horizontal axis shows the retention time (min), and the vertical axis shows the relative intensity ($\mu$V).

Next, these collected fractions were placed in a dialysis pack, and dialyzed with 0.1 M ammonium hydrogencarbonate (pH8.0). Thereafter, the liquid in the pack was collected, and subjected to an enzyme treatment (cleavage treatment) at 37° C. for 18 hours in an ammonium hydrogencarbonate buffer (pH7.8) to which an appropriate amount of endoprotease Glu-C was added. Thereafter, the liquid treated with enzyme was collected and subjected to a reverse phase high speed liquid chromatography. More specifically, the liquid treated with enzyme was applied to a reverse phase column (Wakosil-II SC518 HG manufactured by Wako Pure Chemical Industries Ltd.) having a size of 4.6×250 mm, and reverse phase chromatography was performed with A solution: 0.05 vol % TFA-containing diluted water; B solution: 0.05 vol % TFA-containing 90 vol % acetonitrile solution, gradient: 100% A solution to 100% B solution for 40 minutes) at a flow rate of 1 mL/min, using RP-HPLC (JASCO Pump System, pump: PU-980, UV detector:UV-970) of JASCO Corporation. As a result, the peak that appeared to be the targeted peptide fragment was detected in the fraction eluted from the column when about 20 minutes passed since the elution start (FIG. 8A). In other words, the position (elution period) of this peak is the same as when a polypeptide (100 µl of a sample of 0.1 mg/mL) of a chemically synthesized (sample 17) was applied to the same column and eluted in the same conditions (FIG. 8B).

Figure 6:
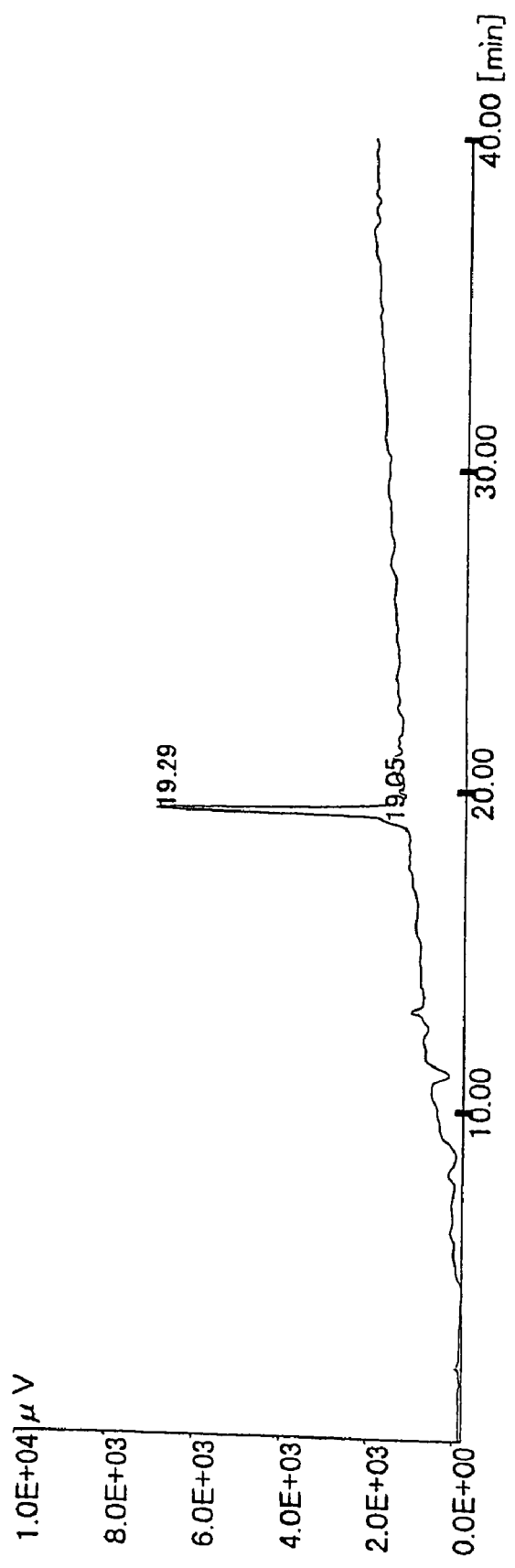
FIG. 6 is a chromatogram showing the results of analyzing a sample obtained by treating and purifying a fusion protein derived from a recombinant E. coli by several processes by reverse phase chromatograph, where the horizontal axis shows the retention time (min), and the vertical axis shows the relative intensity ($\mu$V).
Figure 7:
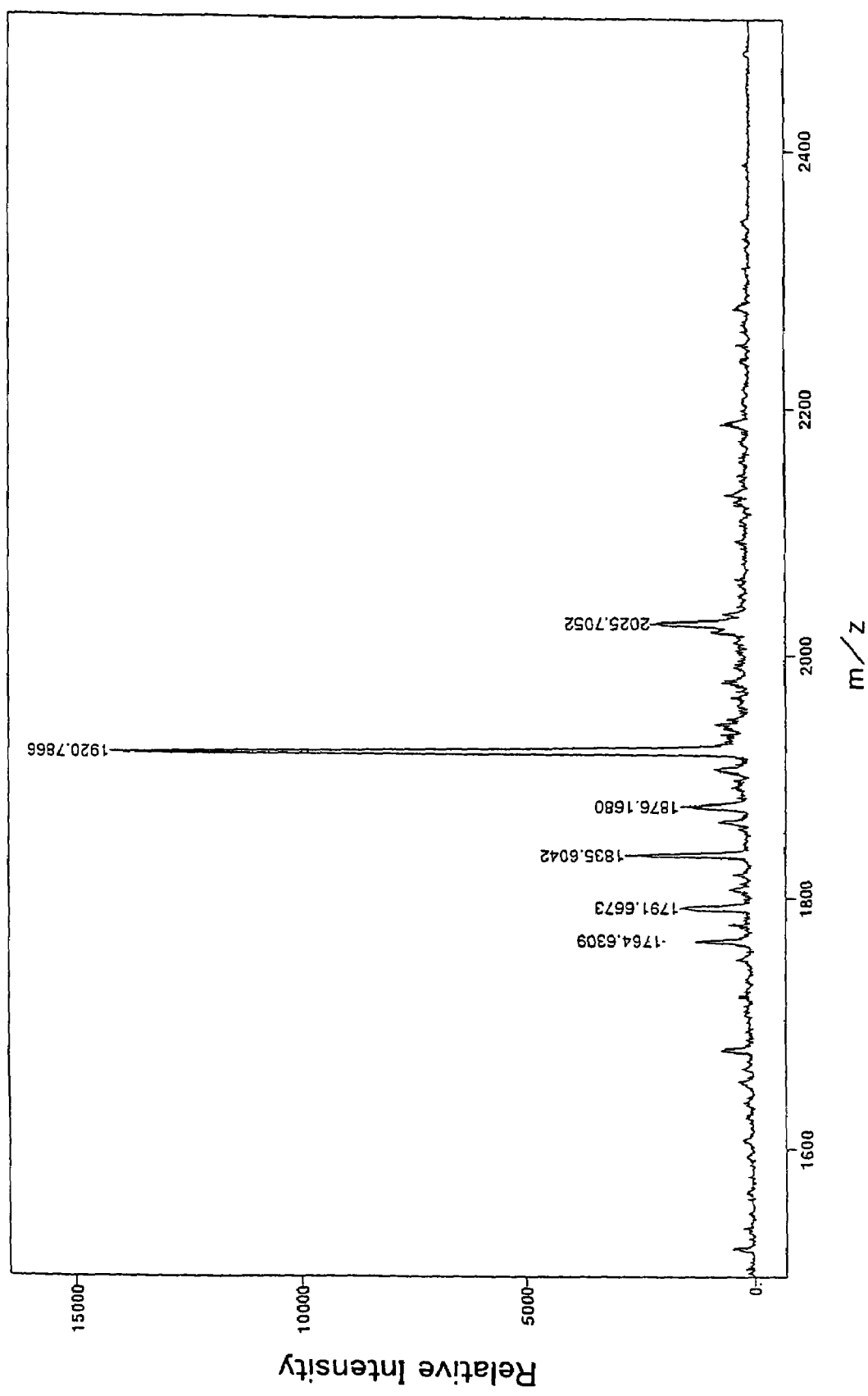
FIG. 7 is a mass spectrum showing the peaks of molecular ions obtained when a polypeptide obtained by purifying a fusion protein derived from a recombinant E. coli by several processes is analyzed with MALDI-TOF MS, where the horizontal axis shows the mass charge ratio (m/z), and the vertical axis shows the relative intensity.

Then, the peak fraction was portioned, and further subjected to reverse phase chromatography. More specifically, the portioned liquid treated with enzyme was applied to a reverse phase column (Lichrospher RP-18: Agilent Technologies) having a size of 4.6×150 mm, and reverse phase chromatography was performed with A solution: 0.15 vol % TFA-containing diluted water; B solution: 0.1 vol % TFA-containing acetonitrile, gradient: 100% A solution to 50% A solution/50% B solution for 40 minutes) at a flow rate of 1 mL/min, using RP-HPLC (JASCO Pump System, pump: PU-980, UV detector:UV-970) of JASCO Corporation. As a result, as shown in FIG. 6, a single peak that appeared to be the targeted peptide fragment was detected in the fraction eluted from the column when about 20 minutes passed since the elution start. Furthermore, the molecular weight of the peptide contained in this peak fraction was determined based on MALDI-TOF MS, using Voyager DE RP (trademark) manufactured by PerSeptive Biosystems (FIG. 7). As a result, the determined molecular weight (1920.78) was equal to the theoretical molecular weight (1920.51) based on the amino acid sequence.

Then, by the same method as in Example 2, the antimicrobial activities (MIC) of the polypeptide purified by the reverse phase chromatography were examined. Table 4 shows the results.

TABLE 4

| | antimicrobial activity (µM) | | | |
| | E. coli | | S. aureus | |
| sample | after 24h | after 48h | after 24h | after 48h |
| purified polypeptide | 3.9 | 3.9 | 3.9 | 7.8 |
| sample 17 (chemically synthesized product) | 3.9 | 3.9 | 3.9 | 3.9 |
| comparative sample 1 | >500 | >500 | >500 | >500 |
| comparative sample 2 | >500 | >500 | >500 | >500 |

As seen from the results shown in Table 4, the polypeptide separated and purified from a recombinant *E. coli* exhibits high antimicrobial activities than the control polypeptide (comparative samples 1 and 2 in Example 2), and the MIC value thereof was equal to that of the polypeptide (sample 17 as above) of the same amino acid sequence produced by chemical synthesis.

Specific examples of the present invention have been described above, but they are only illustrative and not limiting the scope of the claims. All changes and modifications from the specific examples illustrated above are intended to be embraced in the techniques disclosed in the appended claims.

The technical elements described in the specification or the drawings can exhibit technical usefulness, either alone or in combination, and combinations are not limited to those described in the claims as filed. The techniques illustrated in the specification or the drawings can achieve a plurality of purposes at the same time, and achieving only one of them has technical usefulness.

The invention claimed is:

1. A pharmaceutical composition for use in preventing or treating bacterial infections comprising:
   an artificially synthesized antimicrobial polypeptide containing at least one amino acid sequence selected from the group consisting of SEQ ID NOS: 84, 85, 86, 87, 88, 89, 90 and 91; and
   a pharmaceutically acceptable carrier.

2. The composition according to claim 1, wherein the polypeptide is C-terminally amidated.

3. A method for producing a pharmaceutical composition comrprising:
   synthesizing a polypeptide containing at least one amino acid sequence selected from the group consisting of SEQ ID NOS: 84, 85, 86, 87, 88, 89, 90 and 91; and
   mixing the synthesized polypeptide with at least one pharmaceutically acceptable carrier.

4. The method of claim 3, wherein the polypeptide is C-terminally amidated.

* * * * *